United States Patent
Mori et al.

(10) Patent No.: US 8,050,381 B2
(45) Date of Patent: Nov. 1, 2011

(54) MEDICAL X-RAY IMAGING SYSTEM

(75) Inventors: Harumichi Mori, Hamamatsu (JP);
Ryuji Kyushima, Hamamatsu (JP);
Kazuki Fujita, Hamamatsu (JP)

(73) Assignee: Hamamatsu Photonics K.K.,
Hamamatsu-shi, Shizuoka (JP)

( * ) Notice: Subject to any disclaimer, the term of this patent is extended or adjusted under 35 U.S.C. 154(b) by 106 days.

(21) Appl. No.: 12/428,236

(22) Filed: Apr. 22, 2009

(65) Prior Publication Data

US 2009/0268867 A1   Oct. 29, 2009

Related U.S. Application Data

(60) Provisional application No. 61/144,533, filed on Jan. 14, 2009, provisional application No. 61/151,548, filed on Feb. 11, 2009.

(30) Foreign Application Priority Data

Apr. 24, 2008 (JP) ............................. P2008-114148
Feb. 6, 2009 (JP) ............................. P2009-026471

(51) Int. Cl.
*A61B 6/14* (2006.01)
*G21K 4/00* (2006.01)
*H05G 1/58* (2006.01)

(52) U.S. Cl. ............................. 378/39; 378/38; 378/191

(58) Field of Classification Search .................... 378/17, 378/19, 20, 38, 39, 191, 210; 250/370.01, 250/370.08, 370.09, 370.11, 370.14, 371

See application file for complete search history.

(56) References Cited

U.S. PATENT DOCUMENTS

| | | | | |
|---|---|---|---|---|
| 5,744,806 A | * | 4/1998 | Frojd | 250/370.09 |
| 6,118,842 A | | 9/2000 | Arai et al. | |
| 7,534,038 B2 | * | 5/2009 | Rotondo et al. | 378/205 |
| 7,773,720 B2 | * | 8/2010 | Honjo et al. | 378/19 |
| 2001/0038075 A1 | * | 11/2001 | Morishita | 250/370.08 |
| 2006/0182224 A1 | | 8/2006 | Besson | |
| 2009/0232275 A1 | * | 9/2009 | Spartiotis et al. | 378/40 |
| 2010/0172462 A1 | * | 7/2010 | Tancredi et al. | 378/4 |

FOREIGN PATENT DOCUMENTS

| | | |
|---|---|---|
| JP | H9-122118 | 5/1977 |
| JP | H7-148163 | 6/1995 |
| JP | H11-318886 | 11/1999 |
| JP | 2006/109808 | 10/2006 |
| JP | 2006-263225 | 10/2006 |
| WO | WO 01/66012 | 9/2001 |
| WO | WO 2007/046372 | 4/2007 |

\* cited by examiner

*Primary Examiner* — Anastasia Midkiff
(74) *Attorney, Agent, or Firm* — Drinker Biddle & Reath LLP

(57) ABSTRACT

The solid-state image pick-up device (1) includes a photodetecting section (10) which is formed by two-dimensionally aligning M×N (M and N are integers not less than 2) pixels in M rows and N columns and has a rectangular photodetecting surface. This solid-state image pick-up device (1) is supported rotatably by a rotation controlling section, and the rotation controlling section controls the rotation angle of the solid-state image pick-up device (1) so that the row direction or column direction of the photodetecting section (10) becomes parallel to the movement direction (B) of the solid-state image pick-up device (1) in one of the two imaging modes, and both of the row direction and the column direction of the photodetecting section (10) tilt with respect to the movement direction (B) of the solid-state image pick-up device (1) in the other imaging mode of the two imaging modes.

8 Claims, 20 Drawing Sheets

Fig.4
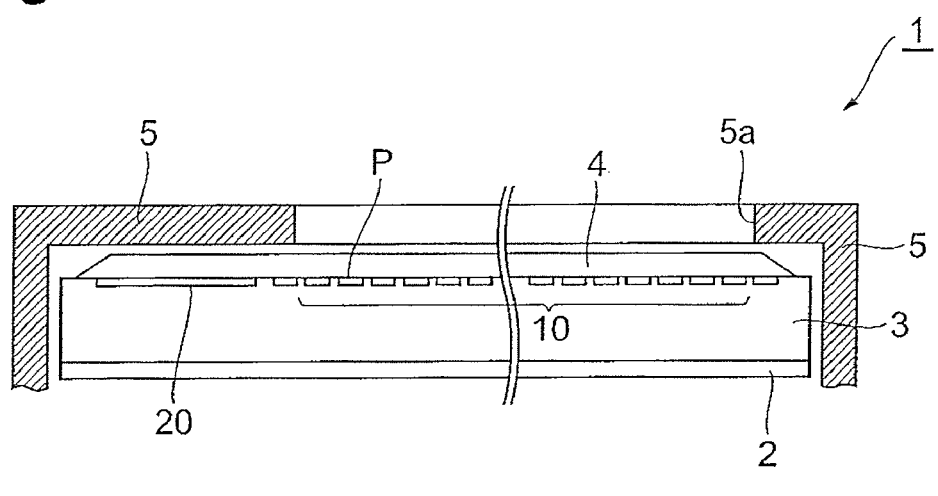
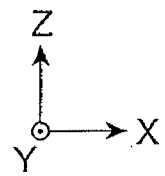

Fig.5
(a)
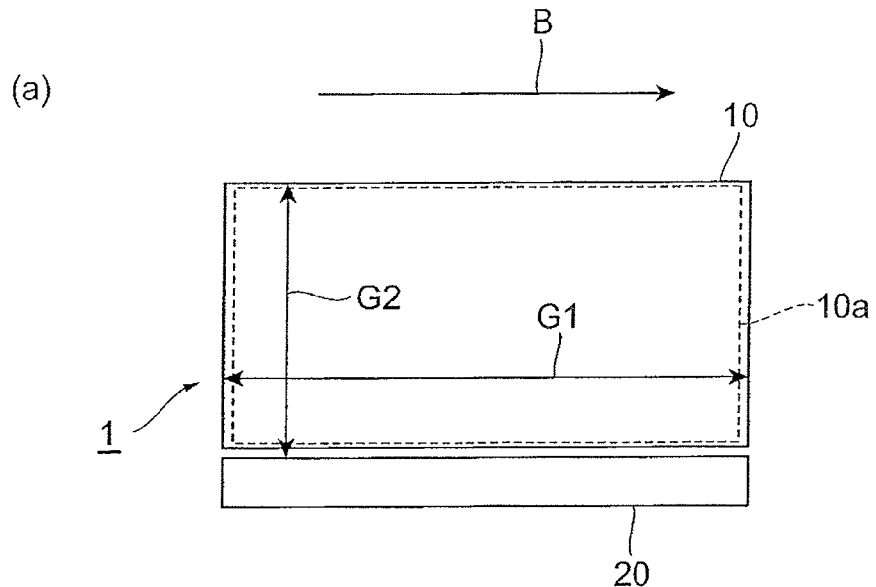
(b)
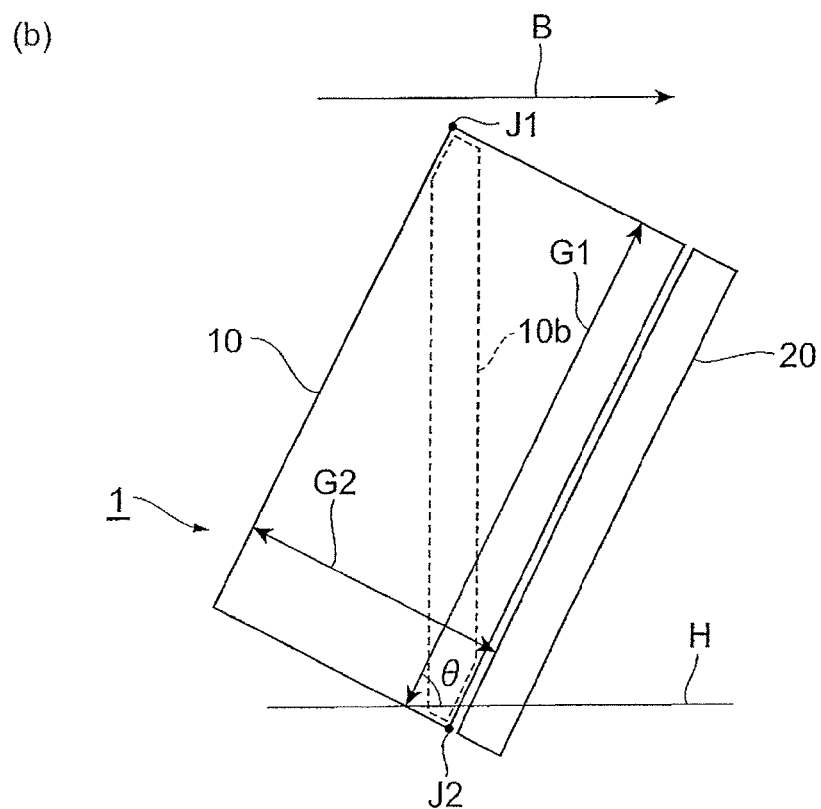

Fig.7
(a)
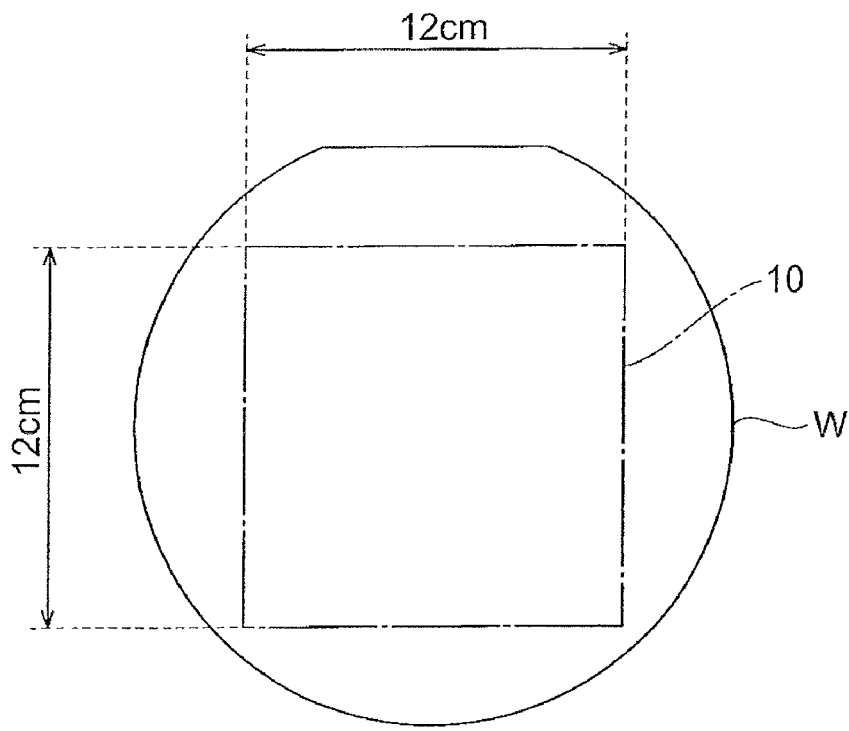
(b)
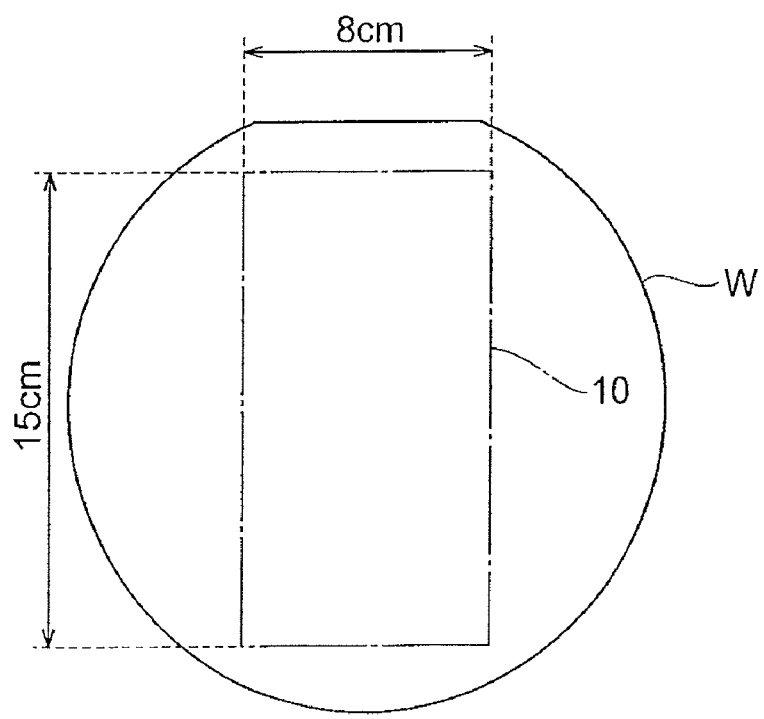

Fig.9
(a)
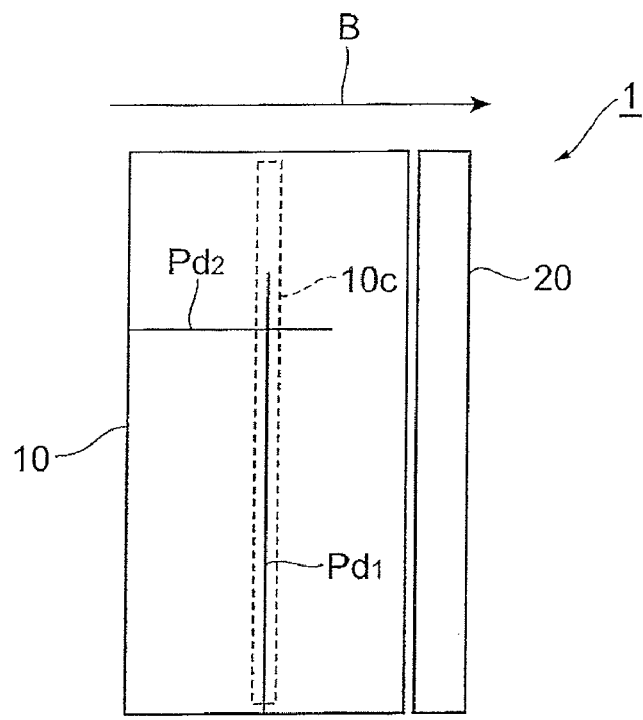
(b)
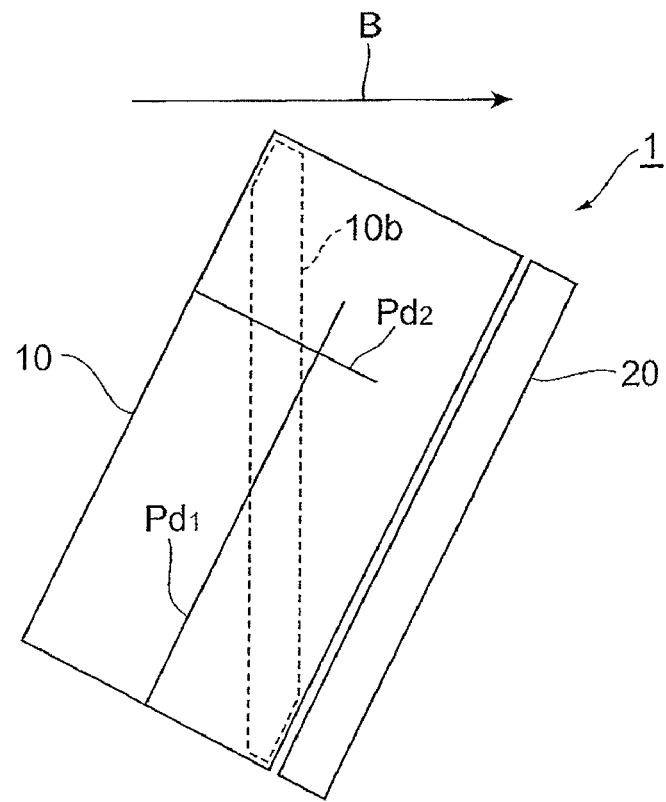

Fig.10
(a)
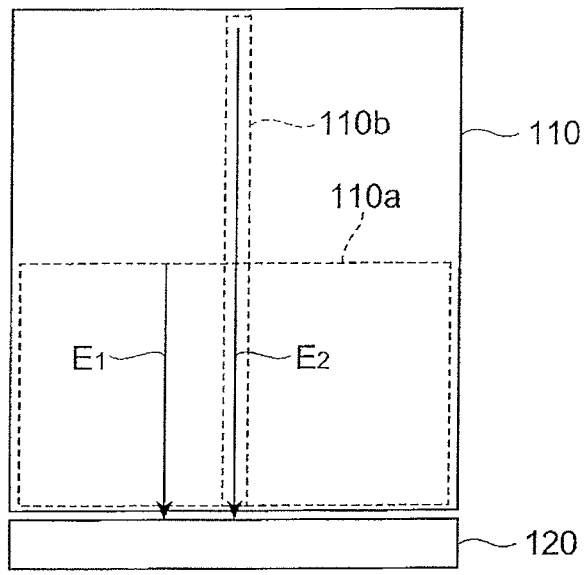
(b)
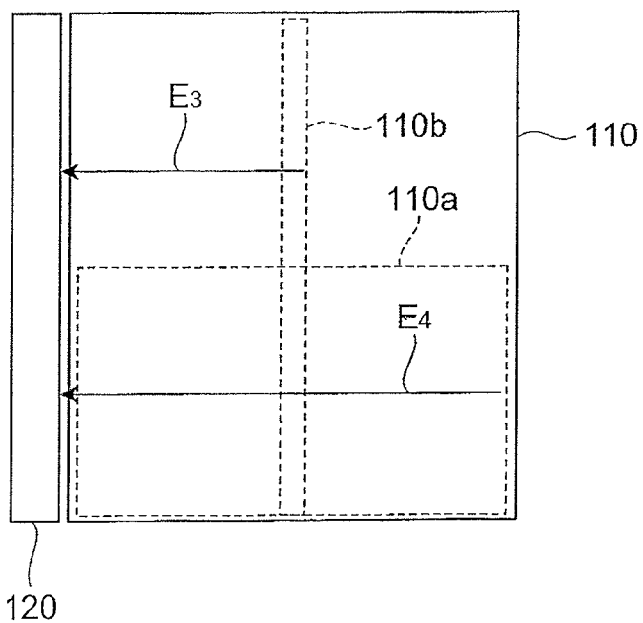

Fig.11
(a)
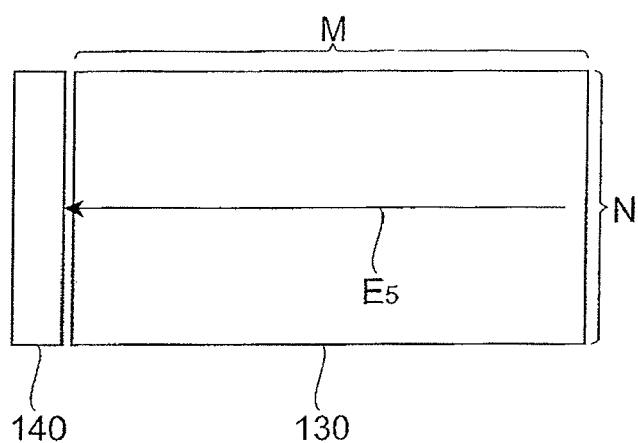
(b)
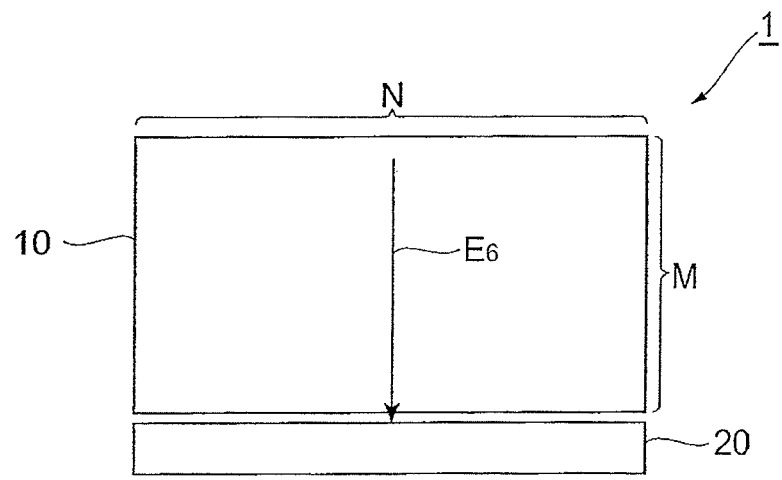

Fig.12
(a)
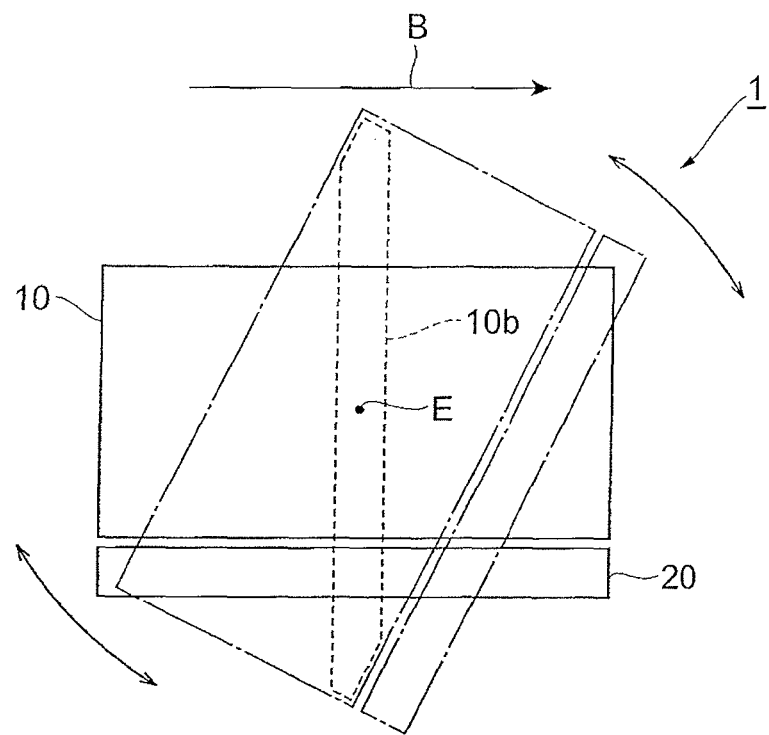
(b)
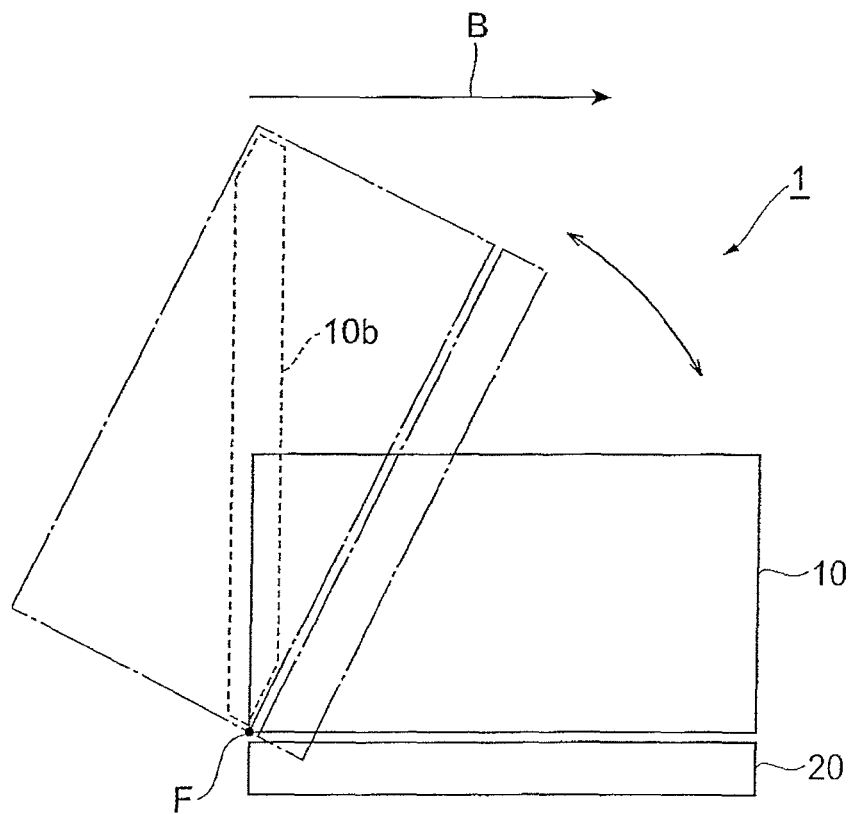

MEDICAL X-RAY IMAGING SYSTEM

BACKGROUND OF THE INVENTION

1. Field of the Invention

The present invention relates to a medical X-ray imaging system.

2. Related Background Art

In medical X-ray photography, in recent years, instead of X-ray sensitive films, X-ray imaging systems using X-ray image pick-up devices have been widely used. Such an X-ray imaging system is convenient such that unlike the X-ray photosensitive film, development is not necessary, and an X-ray image can be confirmed in real time, and is also superior in terms of data storage stability and handling easiness. In X-ray photography for dental diagnosis, such X-ray imaging systems have been increasingly used in various imaging modes for panoramic radiography, cephalometric radiography, and CT.

In the case of a dental X-ray imaging system, the shape of an imaging region required for the X-ray image pick-up device may differ depending on various imaging modes described above. In other words, an imaging region to be used for CT (hereinafter, referred to as a first imaging region) is required to have a sufficient width in the lateral direction, and also required to have a certain width in the up-down direction. An imaging region to be used for panoramic radiography or cephalometric radiography (hereinafter, referred to as a second imaging region) is required to have a sufficient width in the up-down direction. However, when a plurality of X-ray image pick-up devices satisfying these requirements are prepared, the X-ray imaging system becomes large in size, or when changing the imaging mode, the X-ray image pick-up device must be changed and this is troublesome. Therefore, preferably, the requirements on the first and second imaging regions are satisfied by one X-ray image pick-up device.

For example, in International Publication No. WO2006/109808, an X-ray image pick-up device for dental diagnoses having an X-ray generator and an X-ray detector is disclosed. In this X-ray image pick-up device, to selectively generate an X-ray slit beam and an X-ray broad beam, an X-ray is irradiated via a narrow-groove-like slit or a rectangular slit. The X-ray slit beam is used for panoramic radiography or cephalometric radiography, and the X-ray broad beam is used for CT, etc. WO2006/109808 describes that both of the X-ray slit beam which passed through the narrow-groove-like slit and the X-ray broad beam which passed through the rectangular slit are imaged by one solid-state image pick-up device.

As a solid-state image pick-up device to be used for such a medical X-ray imaging system, solid-state image pick-up devices using the CMOS technique are known, and among these, a solid-state image pick-up device using a passive pixel sensor (PPS) type is known. The solid-state image pick-up device using the PPS type has a photodetecting section which includes PPS-type pixels including photodiodes for generating charges corresponding to incident light intensities are two-dimensionally aligned in M rows and N columns, and accumulates charges generated in the photodiode in response to light incidence on each pixel into a capacitive element in an integrating circuit, and outputs a voltage value corresponding to the accumulated charge.

Generally, output terminals of the M pixels in each column are connected to an input terminal of the integrating circuit provided corresponding to the column via a reading wire provided corresponding to the column. Charges generated in the photodiodes of the respective pixels are input into the integrating circuit through the reading wires corresponding to the relevant column from each row successively from the first row to the M-th row, and from the integrating circuit, a voltage value corresponding to the charges is output.

SUMMARY OF THE INVENTION

As described above, in the case of a dental X-ray imaging system, the shape of an imaging region required for the solid-state image pick-up device may differ depending on various imaging modes for panoramic radiography and CT, and preferably, these imaging modes are realized by one solid-state image pick-up device. However, in the configuration described in WO2006/109808, although X-ray beams in these imaging modes are imaged by one solid-state image pick-up device, to set the first imaging region for CT which has a sufficient width in the lateral direction and also has a certain width in the up-down direction and the second imaging region for panoramic radiography which has a sufficient width in the up-down direction within one photodetecting surface, a wide photodetecting surface which has sufficient widths in both of the up-down direction and the lateral direction is necessary. However, due to restrictions in size, etc., of a semiconductor wafer as a material of the photodetecting section of the solid-state image pick-up device, it may be impossible to produce a solid-state image pick-up device with such a wide photodetecting surface.

The present invention was made to solve the above-described problem, and an object thereof is, in a medical X-ray imaging system having at least two imaging modes, to realize the two imaging modes by one solid-state image pick-up device, and restrain an increase in area required for the photodetecting surface of the solid-state image pick-up device.

A medical X-ray imaging system of the present invention includes a solid-state image pick-up device which images an X-ray image while moving around a jaw of an examinee, and has at least two imaging modes, wherein the solid-state image pick-up device includes: a photodetecting section having a rectangular photodetecting surface formed by two-dimensionally aligning M×N pixels (M and N are integers not less than 2) including photodiodes respectively, in M rows and N columns; N reading wires each of which is disposed for each of the columns and connected to the photodiodes included in the pixels of the corresponding column via reading switches; a signal reading section which holds voltage values corresponding to charges input through the reading wires and outputs the held voltage values successively; a controlling section which controls opening and closing operations of the reading switches of the respective pixels, and controls the voltage value output operation in the signal reading section to output voltage values corresponding to the charges generated in the photodiodes of the respective pixels from the signal reading section; and a scintillator which generates scintillation light in response to an incident X-ray and converts the X-ray image into an optical image, and outputs the optical image to the photodetecting section, and the medical X-ray imaging system further includes: a rotation controlling section which supports the solid-state image pick-up device rotatably around an axis line perpendicular to the photodetecting surface, and controls a rotation angle of the solid-state image pick-up device so that, in one imaging mode of the two imaging modes, either a row direction or a column direction of the photodetecting section is along a movement direction of the solid-state image pick-up device, and in the other imaging mode of the two imaging modes, both of the row direction and the column direction of the photodetecting section tilt with respect to the movement direction of the solid-state image pick-up device.

In the medical X-ray imaging system of the present invention, the photodetecting section of the solid-state image pick-up device has a rectangular photodetecting surface, and this solid-state image pick-up device is supported rotatably around the axis line perpendicular to the photodetecting surface by the rotation controlling section. In one imaging mode of the two imaging modes, the rotation angle of the solid-state image pick-up device is controlled so that the row direction or the column direction of the photodetecting section is along the movement direction of the solid-state image pick-up device. When this one imaging mode is, for example, a CT mode, a solid-state image pick-up device having a photodetecting surface which has a sufficient width in either one of the row direction and the column direction and also has a certain width in the other direction is used, and by controlling the rotation angle of the solid-state image pick-up device so that the direction with the sufficient width of the row direction or the column direction is along the movement direction of the solid-state image pick-up device, the above-described first imaging region can be preferably realized.

When the other imaging mode is, for example, a panoramic radiographic mode or a cephalometric radiographic mode, as described above, the second imaging region with a sufficient width in the up-down direction is required. To satisfy this requirement without increasing the area of the photodetecting surface, for example, it is also possible that the longitudinal direction of the photodetecting surface is matched with the up-down direction by rotating the above-described solid-state image pick-up device by 90 degrees. However, in some cases, the width in the up-down direction required for the second imaging region is not satisfied even by the width in the longitudinal direction of the photodetecting surface satisfying the requirement for the first imaging region. For example, in the current CT, the lateral width of the imaging region required generally is approximately 12 cm, however, the up-down width of the imaging region required generally in the panoramic radiography is approximately 15 cm.

Therefore, in the medical X-ray imaging system of the present invention, the rotation angle of the solid-state image pick-up device is controlled so that both of the row direction and the column direction of the photodetecting section tilt with respect to the movement direction of the solid-state image pick-up device in the other imaging mode. The shape of the photodetecting surface is rectangular, so that by thus tilting the photodetecting section with respect to the movement direction of the solid-state image pick-up device, the width in the up-down direction of the photodetecting surface can be increased (to, for example, the length of the diagonal line). In other words, even if the width in the longitudinal direction of the photodetecting surface is shorter than the width in the up-down direction required for the second imaging region, the required width of the second imaging region can be satisfied. Therefore, according to the present invention, in the medical X-ray imaging system having at least two imaging modes, the two imaging modes can be realized by one solid-state image pick-up device, and an increase in area required for the photodetecting surface of the solid-state image pick-up device can be restrained.

It is also possible in the medical X-ray imaging system that the controlling section controls an output operation of the signal reading section so that voltage values are selectively read from the pixels forming an imaging region whose longitudinal direction is in a predetermined direction among the M×N pixels in the other imaging mode, and the predetermined direction tilts with respect to both of the row direction and the column direction of the photodetecting section and intersects the movement direction of the solid-state image pick-up device. Thus, the imaging region which tilts with respect to both of the row direction and the column direction of the photodetecting section and whose longitudinal direction is a direction intersecting the movement direction of the solid-state image pick-up device is preferable as an imaging region in the other imaging mode. When the output operation of the signal reading section is thus controlled, preferably, the predetermined direction is orthogonal to the movement direction of the solid-state image pick-up device, and the imaging region is a region on a diagonal line of the photodetecting section.

It is also possible in the medical X-ray imaging system that, when the controlling section controls the output operation of the signal reading section in the other imaging mode, among voltage values held corresponding to the respective N rows of the photodetecting section, voltage values held corresponding to continuous $N_1$ columns ($N_1 < N$) are output from the signal reading section, and a position of the $N_1$ columns in the photodetecting section shifts by a predetermined number of columns each time of reading a voltage value corresponding to one or a plurality of lines. For example, by thus controlling the output operation of the signal reading section by the controlling section, voltage values can be selectively read from the pixels composing the imaging region whose longitudinal direction is in the predetermined direction.

It is possible in the medical X-ray imaging system that the number of rows M is smaller than the number of columns N in the photodetecting section, and the photodetecting surface has a rectangular shape whose longitudinal direction is in the row direction. In this medical X-ray imaging system, the reading wire is disposed for each column, so that by thus configuring the photodetecting section, the disposition direction of the reading wires and the shorter side direction of the photodetecting surface match each other. Therefore, the number of pixels (photodiodes) from which charges are read through the reading wires in each frame can be reduced, so that the frame rate (the number of frame data to be output per unit time) can be made higher.

It is also possible in the medical X-ray imaging system that a rotation center of the solid-state image pick-up device is positioned at one of four corners of the rectangular photodetecting section, and the solid-state image pick-up device rotates so that the one corner is positioned at a lower jaw side with respect to the examinee in both of the two imaging modes. When the solid-state image pick-up device images an X-ray image while moving around the jaw of the examinee, in many cases, the position of the head of the examinee is fixed by placing the lower jaw of the examinee on a supporting base, and in this case, the reference of the height of the jaw of the examinee is set at the lower end of the jaw. According to this medical X-ray imaging system, the heights of the lower end of the photodetecting surface in the two imaging modes can be matched with each other at the height of the corner as the rotation center. Therefore, the heights of the photodetecting surface in the two imaging modes and the height of the jaw of the examinee can be accurately matched.

It is also possible in the medical X-ray imaging system that in comparison with one imaging mode, in the other imaging mode, the controlling section makes smaller a reading pixel pitch in frame data based on voltage values output from the signal reading section, makes higher a frame rate which is the number of frame data to be output per unit time, and makes larger a gain which is a ratio of an output voltage value to an input charge amount in the signal reading section. Accordingly, operations suitable for the respective imaging modes for CT and panoramic radiography can be realized.

In the medical X-ray imaging system, preferably, the one imaging mode is an imaging mode for CT in dental X-ray photography, and the other imaging mode is an imaging mode for panoramic radiography in dental X-ray photography.

According to the present invention, in a medical X-ray imaging system having at least two imaging modes, the two imaging modes can be realized by one solid-state image pick-up device, and an area required for the photodetecting surface of the solid-state image pick-up device can be made smaller.

BRIEF DESCRIPTION OF THE DRAWINGS

FIG. 4 is a side sectional view of the solid-state image pick-up device 1 along the IV-IV line of FIG. 3;

FIG. 5 is a view showing angular positions of the solid-state image pick-up device 1 and imaging regions in a photodetecting section 10 according to imaging modes. (a) shows an angular position of the solid-state image pick-up device 1 and an imaging region 10a of the photodetecting section 10 in an imaging mode (first imaging mode) such as CT. (b) shows an angular position of the solid-state image pick-up device 1 and an imaging region 10a of the photodetecting section 10 in an imaging mode (second imaging mode) for panoramic radiography or cephalometric radiography;

FIG. 7 is a view showing (a) a state where a square surface is imposed for the photodetecting section 10 on a silicon wafer W, and (b) a state where a rectangle is imposed for the photodetecting section 10 on a silicon wafer W;

FIG. 9 is a view showing (a) defective pixels $Pd_1$ occurring in a certain row and defective pixels $Pd_2$ occurring in a certain column of the photodetecting section 10 when the rotation angle of the solid-state image pick-up device 1 is controlled so that the row direction of the photodetecting section 10 and the movement direction B of the solid-state image pick-up device 1 become orthogonal to each other, and (b) defective pixels $Pd_1$ and $Pd_2$ occurring similar to those in FIG. 9(a) when the rotation angle of the solid-state image pick-up device 1 is controlled so that both of the row direction and the column direction of the photodetecting section 10 tilt with respect to the movement direction B of the solid-state image pick-up device 1;

FIG. 10 is a view showing a charge reading method in a conventional solid-state image pick-up device to be used without rotating the photodetecting section. (a) shows a case where the signal reading section 120 is disposed along the longitudinal direction of an imaging region 110a. (b) shows a case where the signal reading section 120 is disposed along the longitudinal direction of an imaging region 110b;

FIG. 11 is a view showing (a) a charge reading method in a case where a signal reading section 140 is disposed along the shorter side direction of a photodetecting section 130, (b) a charge reading method of the solid-state image pick-up device 1 of the first embodiment;

FIG. 12 is a view showing rotation of the photodetecting section 10 according to the position of the rotation center (axis line C shown in FIG. 1) of the solid-state image pick-up device 1. (a) shows a case where the center E of the photodetecting section 10 is set as the rotation center of the solid-state image pick-up device 1. (b) shows a case where one corner F among four corners of the rectangular photodetecting section 10 is set as the rotation center of the solid-state image pick-up device 1, and the solid-state image pick-up device 1 is rotated so that the corner F is positioned lower than the other corners throughout the first imaging mode and the second imaging mode;

DESCRIPTION OF THE PREFERRED EMBODIMENTS

Figure 1:
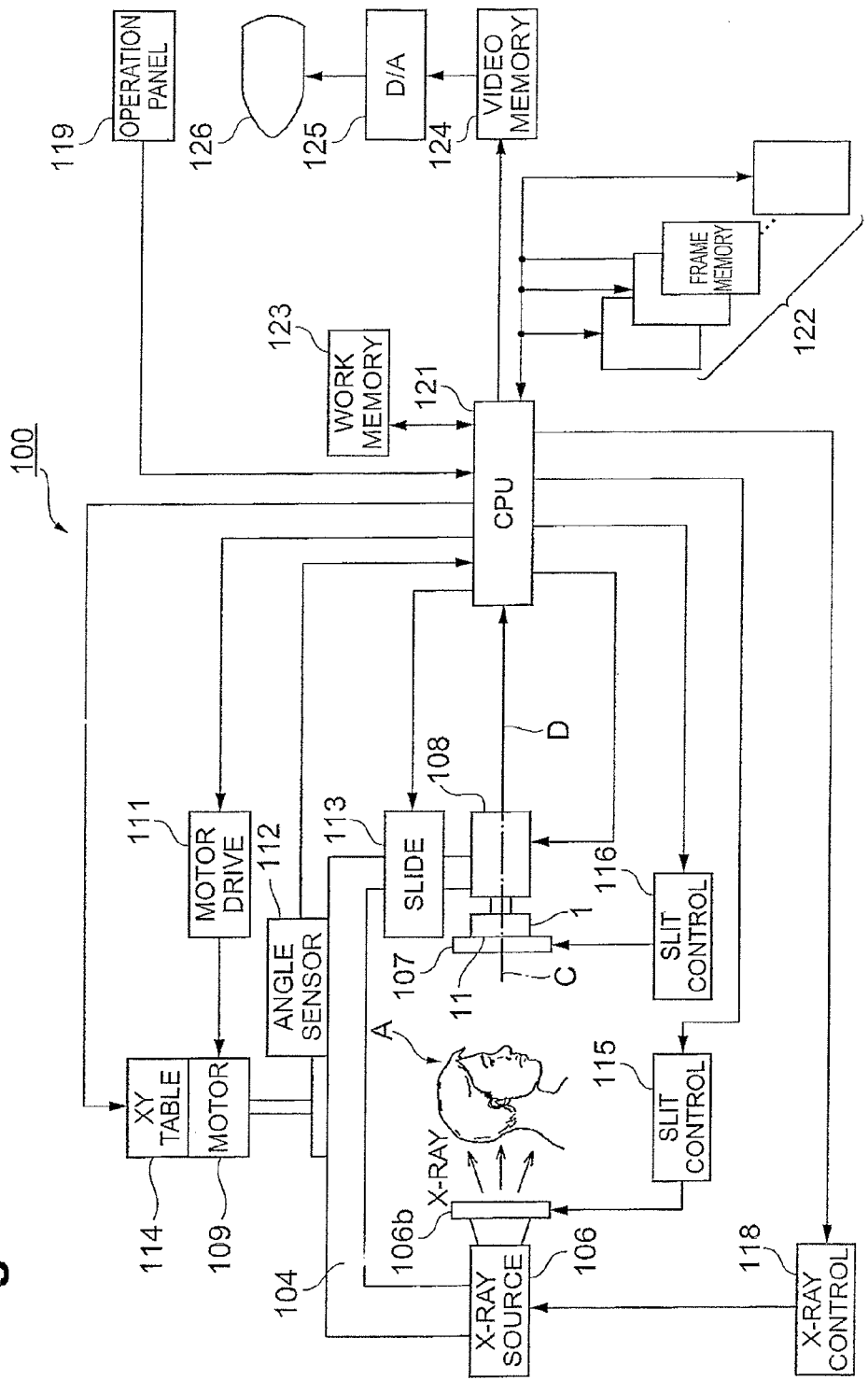
FIG. 1 is a configurational view of an X-ray imaging system 100 of a first embodiment.

Hereinafter, a best mode for carrying out the present invention will be described with reference to the accompanying drawings. In the description of the drawings, identical elements are attached with the same reference numerals, and overlapping description is omitted.

FIG. 1 is a view showing a configuration of a medical X-ray imaging system 100 as an embodiment of the present invention. The X-ray imaging system 100 of the present embodiment has imaging modes for panoramic radiography, cephalometric radiography, and CT, etc., to be used mainly for dental purposes, and images an X-ray image of the jaw of an examinee. The X-ray imaging system 100 includes a solid-state image pick-up device and an X-ray generator, and images an X-ray which is output from the X-ray generator and transmitted through a subject A (that is, the jaw of an examinee) by the solid-state image pick-up device.

The X-ray imaging system 100 shown in this figure includes the solid-state image pick-up device 1, the X-ray generator 106, and a rotation controlling section 108 which supports rotatably the solid-state image pick-up device 1.

The X-ray generator 106 generates an X-ray toward the subject A. The irradiation field of the X-ray generated from the X-ray generator 106 is controlled by a primary slit plate 106b. An X-ray tube is installed inside the X-ray generator 106, and by adjusting the conditions such as a tube voltage, a tube current, and an energization time of the X-ray tube, the X-ray irradiation amount onto the subject A is controlled. The X-ray generator 106 outputs an X-ray with a predetermined expansion angle in a certain imaging mode according to control of the opening range of the primary slit plate 106b, and in other imaging modes, outputs an X-ray with an expansion angle smaller than the predetermined expansion angle.

The solid-state image pick-up device 1 is a CMOS solid-state image pick-up device including a plurality of pixels two-dimensionally aligned, and converts an X-ray image which was passed through the subject A into image data D. In front of the solid-state image pick-up device 1, a secondary slit plate 107 for limiting the X-ray incidence region is provided. The rotation controlling section 108 supports the solid-state image pick-up device 1 rotatably around the axis line C perpendicular to the photodetecting surface 11 of the solid-state image pick-up device 1, and rotates the solid-state image pick-up device 1 to a predetermined angular position according to the imaging mode for CT, panoramic radiography, or cephalometric radiography.

The X-ray imaging system 100 further includes a swiveling arm 104. The swiveling arm 104 holds the X-ray generator 106 and the solid-state image pick-up device 1 so as to oppose these to each other, and swivels these around the subject A at the time of CT, panoramic radiography, or cephalometric radiography. In the case of linear tomography, a slide mechanism 113 for linearly displacing the solid-state image pick-up device 1 with respect to the subject A is provided. The swiveling arm 104 is driven by an arm motor 109 forming a turning table, and the rotation angle thereof is detected by an angle sensor 112. The arm motor 109 is mounted on a movable portion of an XY table 114, and a rotation center thereof is arbitrarily adjusted within a horizontal plane.

Image data D output from the solid-state image pick-up device 1 is temporarily taken into a CPU (Central Processing Unit) 121, and then stored in a frame memory 122. From image data stored in the frame memory 122, a tomographic image along an arbitrary cross-sectional plane or a panoramic image is reproduced by predetermined arithmetic operation processing. The reproduced tomographic image or panoramic image is output to the video memory 124, converted into analog signals by a D-A converter 125, and then displayed on an image display 126 such as CRT (cathode ray tube), and used for various diagnoses.

To the CPU 121, a work memory 123 necessary for signal processing is connected, and an operation panel 119 including a panel switch and an X-ray irradiation switch, etc., is further connected. The CPU 121 is connected to a motor drive circuit 111 which drives the arm motor 109, slit control circuits 115 and 116 which control opening ranges of the primary slit plate 106b and the secondary slit plate 107, and an X-ray control circuit 118 which controls the X-ray generator 106, and further outputs a clock signal for driving the solid-state image pick-up device 1. The X-ray control circuit 118 performs feedback control of an X-ray irradiation amount onto the subject based on signals imaged by the solid-state image pick-up device 1.

Figure 2:
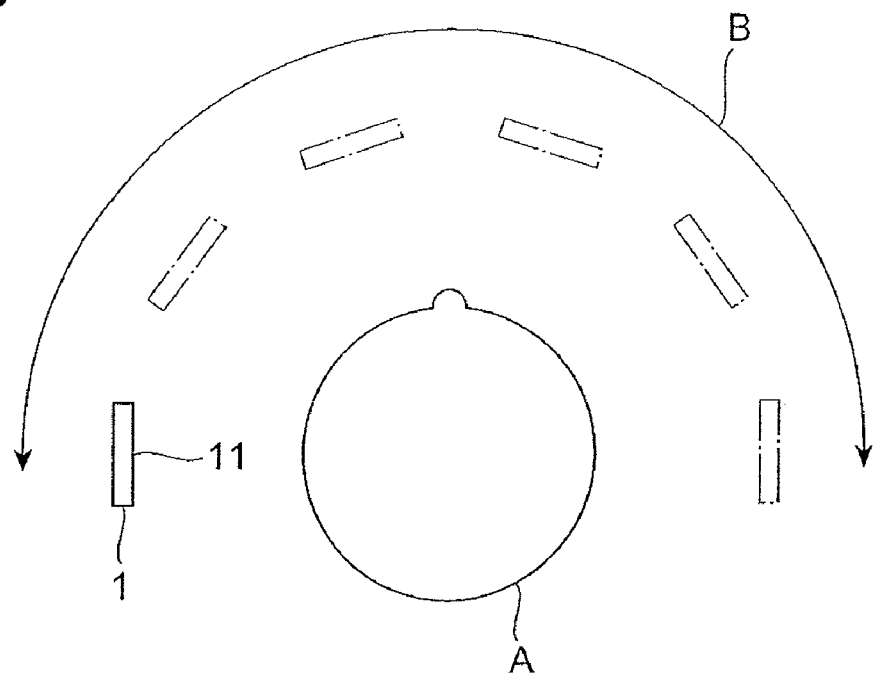
FIG. 2 is a view showing swiveling movement of a solid-state image pick-up device 1 around a subject A as viewed from above the subject A (jaw of an examinee)

FIG. 2 is a view showing swiveling movement of the solid-state image pick-up device 1 around the subject A as viewed from above the subject A (the jaw of the examinee). In this figure, the locus of the solid-state image pick-up device 1 is shown by alternate long and short dashed lines. The solid-state image pick-up device 1 images an X-ray image which passed through the subject A while moving in the circumferential direction (arrow B in the figure) along the horizontal plane around the subject A by the swiveling arm 104. At this time, the orientation of the solid-state image pick-up device 1 is set so that the photodetecting surface 11 of the solid-state image pick-up device 1 is always opposed to the subject A.

Figure 3:
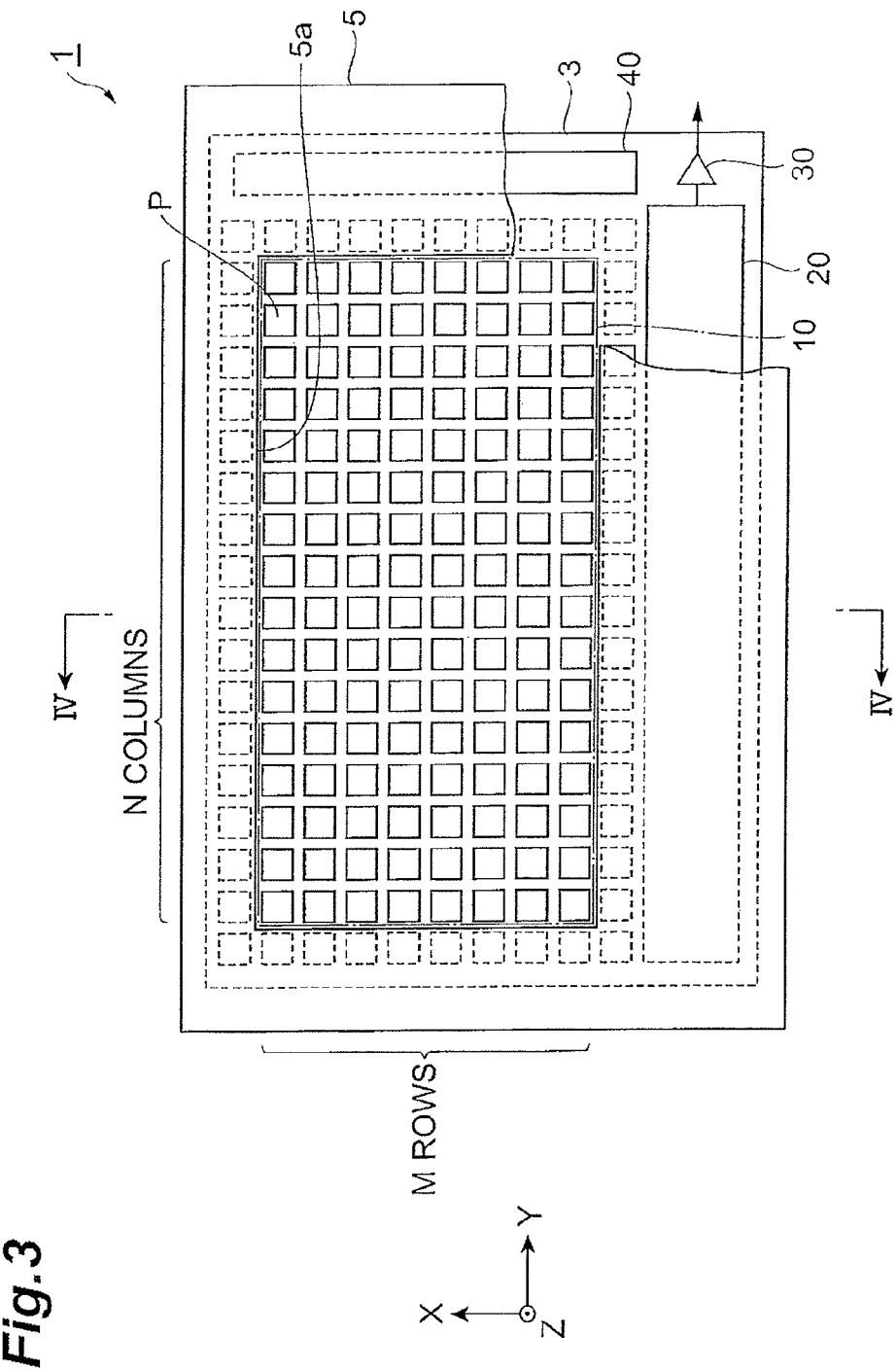
FIG. 3 is a partially cut-away plan view of the solid-state image pick-up device 1.

FIG. 3 and FIG. 4 are views showing a configuration of the solid-state image pick-up device 1 in the present embodiment. FIG. 3 is a partially cut-away plan view of the solid-state image pick-up device 1, and FIG. 4 is a sectional side view of the solid-state image pick-up device 1 along the IV-IV line of FIG. 3. In FIG. 3 and FIG. 4, an XYZ orthogonal coordinate system is also shown for easy understanding. As shown in FIG. 3, the solid-state image pick-up device 1 includes a photodetecting section 10, a signal reading section 20, an A/D converter 30, and a scanning shift register 40 which are formed in a principal surface of a semiconductor substrate 3. The photodetecting section 10, the signal reading section 20, the A/D converter 30, and the scanning shift register 40 may be formed on semiconductor substrates separate from each other. As shown in FIG. 4, in addition to the semiconductor substrate 3, the solid-state image pick-up device 1 includes a planar base material 2, a scintillator 4, and an X-ray shield 5. The semiconductor substrate 3 is stuck onto the base material 2, and the scintillator 4 is disposed on the semiconductor substrate 3. The scintillator 4 generates scintillation light according to an incident X-ray and converts an X-ray image into an optical image, and outputs this optical image to the photodetecting section 10. The scintillator 4 is installed so as to cover the photodetecting section 10, or is provided on the photodetecting section 10 by vapor deposition. The X-ray shield 5 is made of a material with a very low X-ray transmittance such as lead. The X-ray shield 5 covers a peripheral edge portion of the semiconductor substrate 3, and prevents X-ray incidence on the signal reading section 20, etc.

The photodetecting section 10 is formed by two-dimensionally aligning M×N pixels in M rows and N columns. In FIG. 3, the column direction matches the X-axis direction, and the row direction matches the Y-axis direction. M and N are integers not less than 2, and preferably, satisfy M<N. In other words, preferably, the number of pixels P in the row direction in the photodetecting section 10 is larger than the number of pixels P in the column direction. In this case, the photodetecting surface of the photodetecting section 10 has a rectangular shape whose longitudinal direction is in the row direction (Y-axis direction), and whose shorter side direction is in the column direction (X-axis direction). The pixels P are aligned at, for example, 100-micrometer pitches, and are a PPS type and have a common configuration.

In the semiconductor substrate 3, pixels are also formed at the periphery of the photodetecting section 10, however, these pixels are covered by the X-ray shield 5 and light is not made incident thereon and charges are not generated, so that these pixels do not contribute to imaging. The photodetecting section 10 of the present embodiment include M×N pixels P two-dimensionally aligned in M rows and N columns as effective pixels for imaging. In other words, the region which becomes the photodetecting section 10 in the semiconductor substrate 3 of the present embodiment is regulated by the opening 5a of the X-ray shield 5.

The signal reading section 20 holds voltage values corresponding to the amounts of charges output from the respective pixels P of the photodetecting section 10, and outputs the held voltage values successively. The A/D converter 30 inputs the voltage values output from the signal reading section 20, and applies A/D conversion processing to the input voltage values (analog values) and outputs digital values corresponding to the input voltage values. The scanning shift register 40 controls the pixels P so that the charges accumulated in the respective pixels P are successively output to the signal reading section 20 from each row.

The X-ray imaging system 100 including this solid-state image pick-up device 1 has imaging modes for CT, panoramic radiography, and cephalometric radiography as described above. The solid-state image pick-up device 1 is supported by the rotation controlling section 108 so as to rotate around the axis line perpendicular to the photodetecting surface, and is controlled to a predetermined angular position corresponding to the imaging mode. The solid-state image pick-up device 1 has a function for changing the imaging region in the photodetecting section 10 (region which contributes to imaging data in the photodetecting section 10) according to the imaging mode.

Here, FIG. 5 is a view showing the angular positions of the solid-state image pick-up device 1 and the imaging regions in the photodetecting section 10 according to the imaging modes. FIG. 5(*a*) shows an angular position of the solid-state image pick-up device 1 and an imaging region 10*a* of the photodetecting section 10 in the imaging mode for CT (first imaging mode). FIG. 5(*b*) shows an angular position of the solid-state image pick-up device 1 and an imaging region 10*b* of the photodetecting section 10 in the imaging mode for panoramic radiography or cephalometric radiography (second imaging mode). In FIGS. 5(*a*) and (*b*), the arrow B shows a movement direction of the solid-state image pick-up device 1 moved by the swiveling arm 104 (see FIG. 1).

As shown in FIG. 5(*a*), in the first imaging mode for CT, the rotation angle of the solid-state image pick-up device 1 is controlled so that one of the row direction (arrow G1 in the figure) and the column direction (arrow G2 in the figure) of the photodetecting section 10 is along the movement direction B, more preferably, the longitudinal direction (row direction G1 in the present embodiment) of the photodetecting section 10 becomes parallel to the movement direction B. At this time, the imaging region 10*a* is composed of all pixels P in the M rows and N columns of the photodetecting section 10. In other words, the widths in the row direction and the column direction of the imaging region 10*a* are the same as those of the photodetecting section 10.

As shown in FIG. 5(*b*), in the second imaging mode for panoramic radiography or cephalometric radiography, the rotation angle of the solid-state image pick-up device 1 is controlled so that both of the row direction G1 and the column direction G2 of the photodetecting section 10 tilt with respect to the movement direction B of the solid-state image pick-up device 1. In other words, in this second imaging mode, the angle θ between the row direction G1 or column direction G2 of the photodetecting section 10 and a swiveling plane H of the solid-state image pick-up device 1 satisfies 0°<θ<90°. Therefore, for example, when the mode changes from the CT mode to the panoramic radiographic mode, the solid-state image pick-up device 1 rotates by the angle θ.

More preferably, the rotation angle of the solid-state image pick-up device 1 is controlled so that one diagonal line of the photodetecting section 10 becomes perpendicular to the swiveling plane H. The angular position of the solid-state image pick-up device 1 in this case is determined by the ratio of the width in the row direction G1 to the width in the column direction G2 of the photodetecting section 10. For example, when the width in the row direction G1 and the width in the column direction G2 are equal to each other, the angle θ with respect to the swiveling plane H of the solid-state image pick-up device 1 is preferably 45 degrees. When the ratio of the width in the row direction G1 to the width in the column direction G2 is 2 to 1, the angle θ with respect to the swiveling plane H of the solid-state image pick-up device 1 is preferably 60 degrees.

The imaging region 10*b* in this case is set as a narrow and long region whose longitudinal direction is in a predetermined direction in the photodetecting section 10. This predetermined direction tilts with respect to both of the row direction G1 and the column direction G2 of the photodetecting section 10, and intersects the movement direction B of the solid-state image pick-up device 1. In the present embodiment, the predetermined direction (longitudinal direction) of the imaging region 10*b* is orthogonal to the movement direction B of the solid-state image pick-up device 1, and is along the diagonal line of the photodetecting section 10. The imaging region 10*b* is set on the diagonal line of the photodetecting section 10. Accordingly, one end of the imaging region 10*b* in the up-down direction of the X-ray imaging system 100, that is, in the direction perpendicular to the swiveling plane H matches the uppermost portion (the vertex J1 of FIG. 5(*b*)) of the photodetecting section 10, and the other end of the imaging region 10*b* in the same direction matches the lowermost portion (the vertex J2 of FIG. 5(*b*)) of the photodetecting section 10. In the second imaging mode, an output operation of the signal reading section 20 is controlled so as to read voltage values selectively from pixels composing this imaging region 10*b* among the M×N pixels of the photodetecting section 10.

Figure 6:
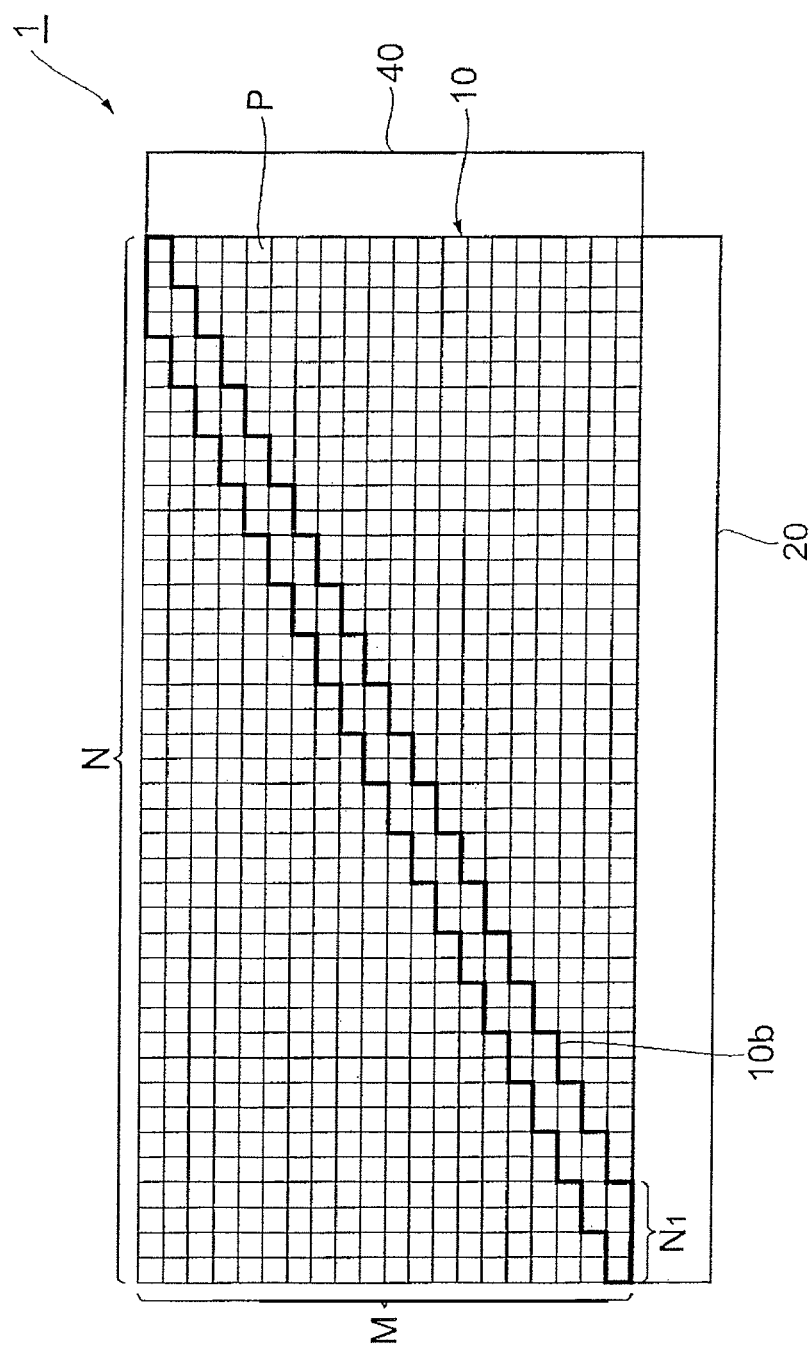
FIG. 6 is a view showing the imaging region 10b shown in FIG. 5(b) in greater detail.

Here, FIG. 6 is a view showing the imaging region 10*b* shown in FIG. 5(*b*) in greater detail. As shown in FIG. 6, the imaging region 10*b* is composed of pixels P of continuous $N_1$ columns ($2<N_1<N$, illustrated by setting $N_1=4$ in FIG. 6) among the pixels P in N columns, and the position of the continuous $N_1$ rows (for example, leading column number) shifts by a predetermined number of columns (2 columns in FIG. 6) in each row. In the solid-state image pick-up device 1, the signal reading section 20 selectively outputs voltage values corresponding to charges output from the pixels P included in this imaging region 10*b*.

The imaging region 10*b* is not limited to the form shown in FIG. 6, and for example, the position of the continuous $N_1$ columns (leading column number) may shift by a predetermined number of columns in each plurality of rows. In the form shown in FIG. 6, even in the rows positioned at both ends in the column direction (first row and M-th row), the imaging region 10*b* is composed of continuous $N_1$ columns. For example, the shapes at both ends of the imaging region 10 can be slightly changed such that in the rows positioned at both ends of the column direction, the number of columns composing the imaging region 10*b* is smaller than $N_1$.

In the X-ray imaging system 100 of the present embodiment, by thus controlling the rotation angle of the solid-state image pick-up device 1, the following effects are obtained. As described above, in the X-ray imaging system 100, the photodetecting section 10 of the solid-state image pick-up device 1 has a rectangular photodetecting surface. In the first imaging mode, the rotation angle of the solid-state image pick-up device 1 is controlled so that the row direction or column direction of the photodetecting section 10 is along the movement direction B of the solid-state image pick-up device 1. When this first imaging mode is, for example, a CT mode, the solid-state image pick-up device 1 having a photodetecting surface which has a sufficient width in one of the row direction and the column direction (row direction in this embodiment) and also has a certain width in the other direction (column direction in the present embodiment) is used, and by controlling the rotation angle of the solid-state image pick-up device 1 so that the direction of the sufficient width in the row direction or the column direction is along the movement direction B of the solid-state image pick-up device 1, the imaging region 10*a* in the first imaging mode can be preferably realized.

When the second imaging mode is a panoramic radiographic mode or cephalometric radiographic mode, an imaging region having a sufficient width in the up-down direction is required. To satisfy this requirement without increasing the area of the photodetecting section 10, for example, it is possible that the longitudinal direction (row direction in this embodiment) of the photodetecting section 10 is matched with the up-down direction by rotating the solid-state image pick-up device 1 by 90 degrees. However, the width in the up-down direction required for the imaging region may not be satisfied even by the width in the longitudinal direction of the photodetecting section 10 satisfying the requirement for the first imaging region 10a.

In the first imaging mode for CT, the entire width of a tooth row must be photographed by one photographing, so that as dimensions of the imaging region, for example, a height (that is, the width in the direction orthogonal to the movement direction B) not less than 8 cm and a lateral width (width in a direction parallel to the movement direction B) not less than 12 cm are required. Therefore, as shown in FIG. 7(a), the dimensions of the photodetecting section 10 are set to, for example, a lateral width of 12 cm and a height of 12 cm by imposing a square surface for the photodetecting section 10 on a substantially circular silicon wafer W, and accordingly, the required dimensions in the first imaging mode are satisfied. However, in the second imaging mode for panoramic radiography, an area from the jaw to the upper and lower tooth rows must be photographed by one photographing, so that as dimensions of the imaging region, for example, a height not less than 15 cm is required (the required lateral width is not less than 7 mm). Therefore, to realize both imaging modes by using one solid-state image pick-up device, if these imaging regions are laid out without rotating the solid-state image pick-up device as in the case of the configuration described in Patent Document 1, a photodetecting section with a height not less than 15 cm and a lateral width not less than 12 cm is required, and a larger silicon wafer is required.

Therefore, in the X-ray imaging system 100, in the second imaging mode, the rotation angle of the solid-state image pick-up device 1 is controlled so that both of the row direction and the column direction of the photodetecting section 10 tilt with respect to the movement direction B of the solid-state image pick-up device 1. The photodetecting section 10 is rectangular, so that by thus tilting the photodetecting section 10 with respect to the movement direction B of the solid-state image pick-up device 1, the width in the up-down direction of the photodetecting section 10 can be widened (to, for example, the length of the diagonal line). For example, when the photodetecting section 10 has dimensions of 12 cm×12 cm, the width in the up-down direction of the imaging region 10b can be increased to 17 cm (that is, to the length of the diagonal line of the photodetecting section 10) at a maximum. Thus, even if the width in the longitudinal direction of the photodetecting section 10 is shorter than the width in the up-down direction required for the imaging region 10b, the required width in the up-down direction of the imaging region 10b can be satisfied. Therefore, according to the X-ray imaging system 100 of the present embodiment, the first imaging mode and the second imaging mode can be realized by one solid-state image pick-up device 1, and an increase in area required for the photodetecting surface of the photodetecting section 10 of the solid-state image pick-up device 1 can be restrained.

As shown in FIG. 7(b), for example, when the photodetecting section 10 on the silicon wafer W has a rectangular shape having dimensions of 15 cm×8 cm, by controlling the rotation angle of the solid-state image pick-up device 1 so that the longitudinal direction of the photodetecting section 10 becomes orthogonal to the movement direction B of the solid-state image pick-up device 1 (that is, without tilting the photodetecting section 10), the required dimensions of the imaging region in the second imaging mode can be satisfied.

However, even when the dimension in the longitudinal direction of the photodetecting section 10 thus satisfies the up-down dimension of the imaging region in the second imaging mode, by tilting the photodetecting section 10 with respect to the movement direction B as in the present embodiment, the width in the up-down direction of the imaging region 10b can be further lengthened. For example, when the photodetecting section 10 has dimensions of 15 cm×8 cm, the width in the up-down direction of the imaging region 10b can be increased to 17 cm (that is, to the length of the diagonal line of the photodetecting section 10) at a maximum.

Figure 8:
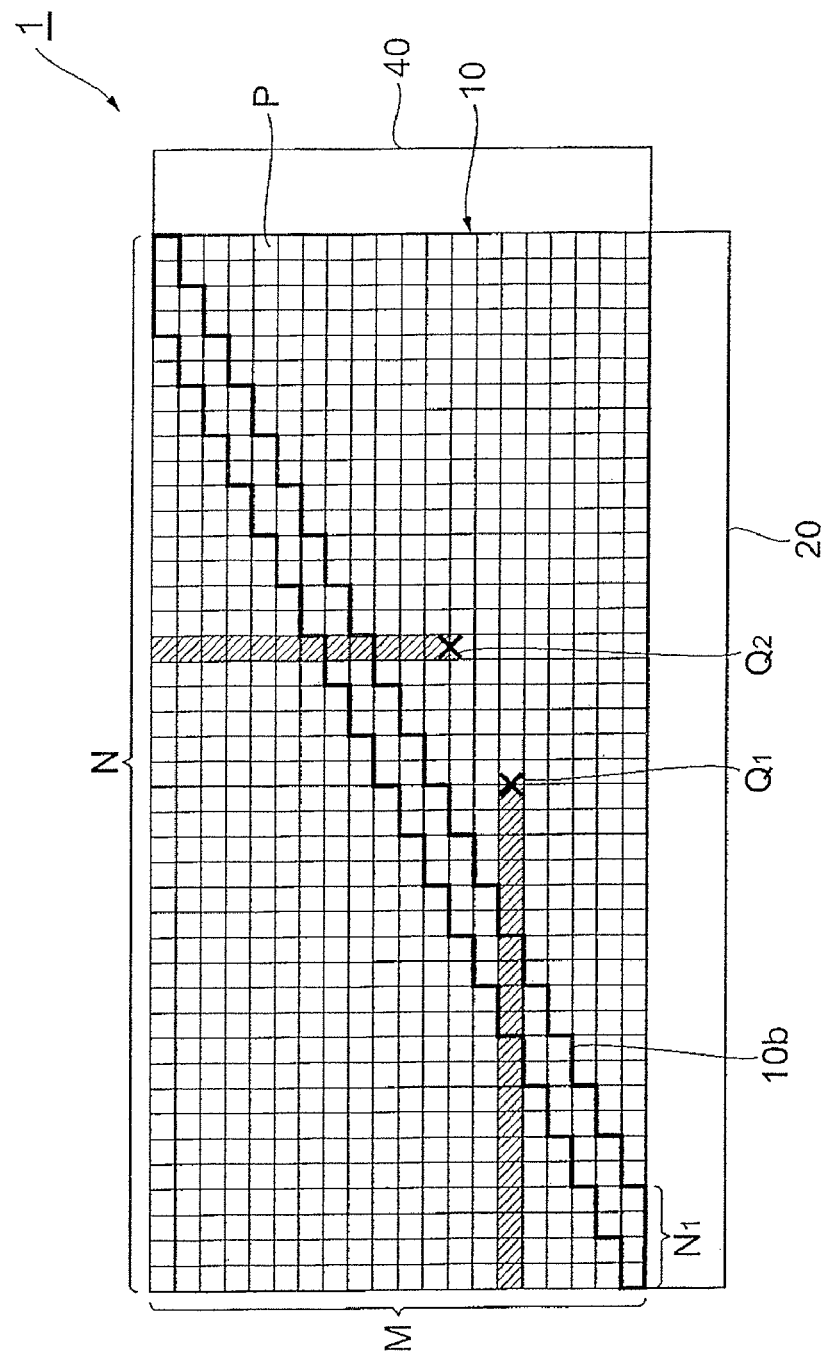
FIG. 8 is a view showing disconnection $Q_1$ occurring in a row selecting wire disposed for each row of the photodetecting section 10 from a scanning shift register 40, and disconnection $Q_2$ occurring in a reading wire disposed for each column from a signal reading section 20.

By tilting the row direction and the column direction of the photodetecting section 10 with respect to the movement direction B, the effects described below can be further obtained. FIG. 8 is a view showing a disconnection $Q_1$ occurring in a row selecting wire (wire for controlling reading of a charge generated in the photodiode of each pixel P in each row) disposed for each row of the photodetecting section 10 from the scanning shift register 40 and a disconnection $Q_2$ occurring in a reading wire (wire for transmitting a charge generated in the photodiode of each pixel P to the signal reading section 20) disposed for each column from the signal reading section 20. When these disconnections $Q_1$ and $Q_2$ occur, the pixels P more distant than the disconnected points from the signal reading section 20 or the scanning shift register 40 in the relevant column or the relevant row (hatched pixels in FIG. 8) become defective pixels (that is, defects) from which charges cannot be read. These defective pixels occur from the occurrence point of the disconnection $Q_1$ or $Q_2$ continuously in the relevant row or the relevant column of the photodetecting section 10.

FIG. 9(a) shows defective pixels $Pd_1$ occurring in a certain row and defective pixels $Pd_2$ occurring in a certain column of the photodetecting section 10 when the rotation angle of the solid-state image pick-up device 1 is controlled so that the row direction of the photodetecting section 10 and the movement direction B of the solid-state image pick-up device 1 become orthogonal to each other. FIG. 9(b) shows defective pixels $Pd_1$ and $Pd_2$ occurring similar to those in FIG. 9(a) when the rotation angle of the solid-state image pick-up device 1 is controlled so that both of the row direction and the column direction of the photodetecting section 10 tilt with respect to the movement direction B of the solid-state image pick-up device 1. The region 10c in the photodetecting section 10 of FIG. 9(a) is a preferable imaging region when the row direction of the photodetecting section 10 and the movement direction B are made orthogonal to each other in the second imaging mode.

As shown in FIG. 9(a), when the rotation angle of the solid-state image pick-up device 1 is controlled so that the row direction of the photodetecting section 10 becomes orthogonal to the movement direction B, the continuing direction of the defective pixels $Pd_2$ and the movement direction B of the solid-state image pick-up device 1 become parallel to each other. Therefore, when the defective pixels $Pd_2$ are also present in the imaging region 10c, the portion corresponding to the defective pixels $Pd_2$ appears as an artifact in the re-composed image obtained after photographing while the solid-state image pick-up device 1 swivels around the examinee.

On the other hand, as shown in FIG. 9(b), when the rotation angle of the solid-state image pick-up device 1 is controlled so that both of the row direction and the column direction of the photodetecting section 10 tilt with respect to the movement direction B of the solid-state image pick-up device 1, the continuing directions of the defective pixels $Pd_1$ and $Pd_2$ and the movement direction B of the solid-state image pick-up device 1 tilt with respect to each other, and never become parallel to each other. Therefore, by photographing while the solid-state image pick-up device 1 swivels around the examinee, the image portions corresponding to the defective pixels $Pd_1$ and $Pd_2$ can be compensated by subsequent frame data, and artifact can be prevented in the re-composed image.

For example, when the solid-state image pick-up device is used without being rotated as in the case of the configuration described in WO2006/109808, as shown in FIG. 10(a) and FIG. 10(b), in the photodetecting section 110, the longitudinal direction of the imaging region 110 in the first imaging mode and the longitudinal direction of the imaging region 110b in the second imaging mode become orthogonal to each other. In this configuration, for example, as shown in FIG. 10(a), when the signal reading section 120 is disposed along the longitudinal direction of the imaging region 110a, the number of pixels per one column in the imaging region 110a becomes smaller (the arrow $E_1$ of FIG. 10(a)), however, the number of pixels per one column in the imaging region 110b becomes larger (the arrow $E_2$ of FIG. 10(a)), and it takes time to read charges in the second imaging mode. Conversely, as shown in FIG. 10(b), when the signal reading section 120 is disposed along the longitudinal direction of the imaging region 110b, the number of pixels per one column in the imaging region 110b becomes smaller (the arrow $E_3$ of FIG. 10(b)), however, the number of pixels per one column in the imaging region 110a becomes larger (the arrow $E_4$ of FIG. 10(b)), and it takes time to read charges in the first imaging mode. Thus, when each imaging region is laid out without rotating the solid-state image pick-up device, it takes time to read charges in either the first imaging mode or the second imaging mode, and the frame rate (the number of frame data to be output per unit time) lowers.

As shown in FIG. 11(a), even in the case where the shape of the photodetecting section 130 is set to be rectangular and the solid-state image pick-up device is used by being rotated, when the number of columns N is smaller than the number of rows M (in other words, when the signal reading section 140 is disposed along the shorter side direction of the photodetecting section 130), in the imaging regions in the first imaging mode and the second imaging mode, the number of pixels per one column becomes larger (the arrow $E_5$ of FIG. 11a)). In this case, it takes time to read charges in both of the first imaging mode and the second imaging mode, and the frame rate lowers.

Therefore, in the solid-state image pick-up device 1 of the present embodiment, when the shape of the photodetecting surface of the photodetecting section 10 is rectangular as shown in FIG. 11(b), preferably, the row direction of this photodetecting section 10 is set as its longitudinal direction, and M<N is satisfied, that is, the number of columns N of the pixels P is larger than the number of rows M. In the solid-state image pick-up device 1, N reading wires (described later) for reading charges from the respective pixels P are disposed for the respective columns, and with this configuration, in both of the first imaging mode and the second imaging mode, the number of pixels P from which charges are read through the reading wires can be reduced (arrow $E_6$ of FIG. 11(b)), the charge readout time can be shortened, and the frame rate can be made higher.

As described above, the solid-state image pick-up device 1 is supported by the rotation controlling section 108, and is controlled to an angular position according to the imaging mode. Here, FIG. 12 is a view showing rotation of the photodetecting section 10 according to the position of the rotation center (axis line C shown in FIG. 1) of the solid-state image pick-up device 1. FIG. 12(a) shows a case where the center E of the photodetecting section 10 is set as the rotation center of the solid-state image pick-up device 1. FIG. 12(b) shows a case where one corner F of the four corners of the rectangular photodetecting section 10 is set as the rotation center of the solid-state image pick-up device 1, and the solid-state image pick-up device 1 is rotated so that the corner F is positioned lower than other corners throughout the first imaging mode and the second imaging mode (that is, the corner F is always positioned at the lower jaw side with respect to the examinee). In FIGS. 12(a) and (b), the figures shown by the solid lines indicate the angular positions of the photodetecting section 10 in the first imaging mode for CT, and the dashed lines indicate angular positions of the photodetecting section 10 in the second imaging mode for panoramic radiography or cephalometric radiography.

The rotation center of the solid-state image pick-up device 1 of the present embodiment can be set at various positions such as the center E of FIG. 12(a) and the corner F of FIG. 12(b), and most preferably, the rotation center of the solid-state image pick-up device 1 is set at the corner F in FIG. 12(b). When the solid-state image pick-up device 1 images an X-ray image while moving around the jaw of an examinee, in many cases, the position of the head of the examinee is fixed by placing the lower jaw of the examinee on a support base, and in this case, the reference of the height of the jaw of the examinee is the lower end of the jaw. By setting the rotation center of the solid-state image pick-up device 1 at the corner F of FIG. 12(b), the heights of the lower end of the photodetecting section 10 in the first imaging mode and the second imaging mode can be matched with each other at the height of the corner F. Therefore, in both of the first imaging mode and the second imaging mode, the height of the photodetecting section 10 and the height of the jaw of the examinee can be matched accurately.

Figure 13:
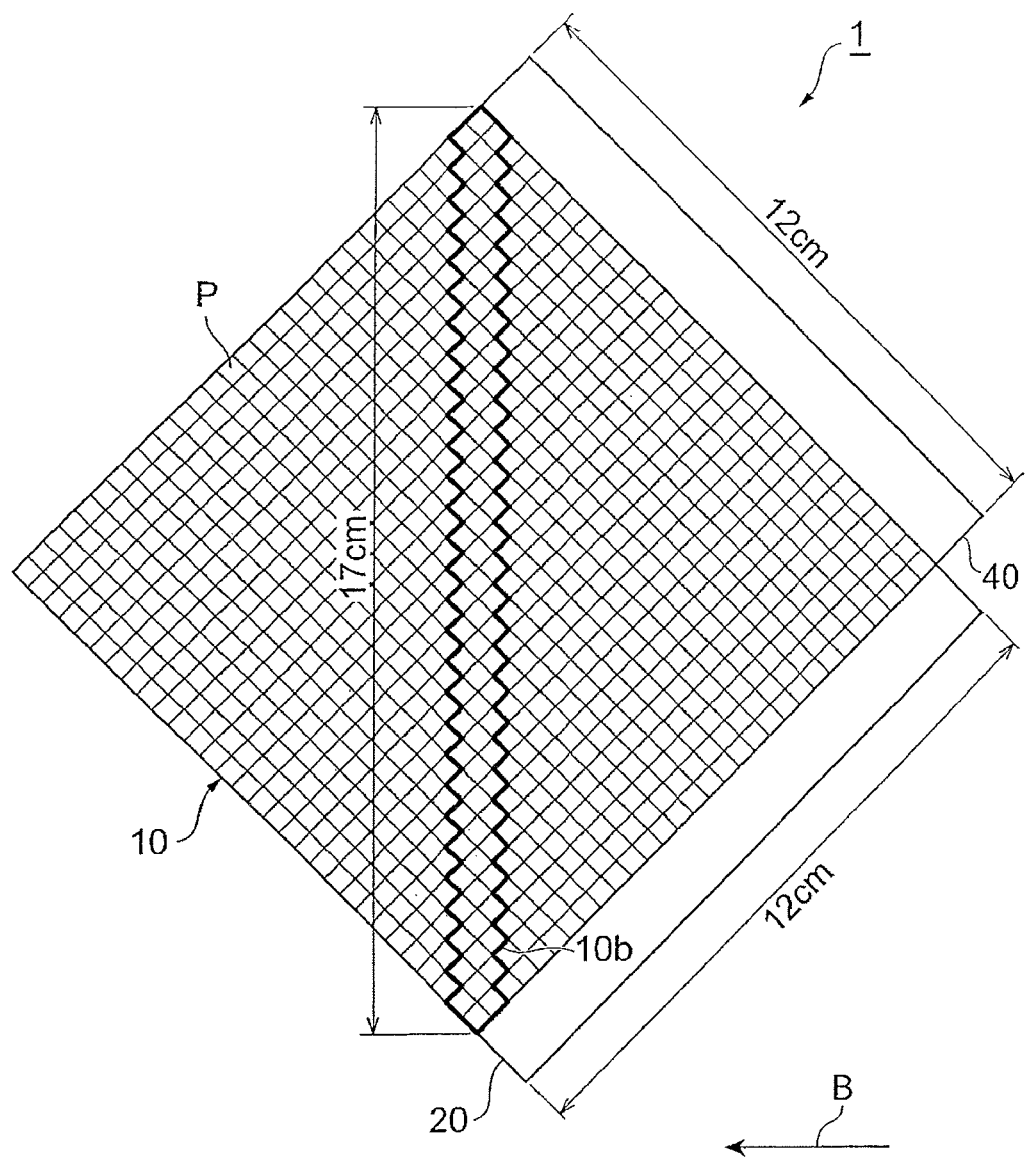
FIG. 13 is a plan view showing a square-shaped photodetecting section 10 and a linear imaging region 10b.

As described above, according to the solid-state image pick-up device 1 of the present embodiment, when the photodetecting section 10 has dimensions of 12 cm×12 cm, by setting the angle θ with respect to the swiveling plane H of the solid-state image pick-up device 1 to 45 degrees, the width in the up-down direction of the imaging region 10b can be increased to 17 cm (that is, to the length of the diagonal line of the photodetecting section 10) at a maximum. Here, FIG. 13 is a plan view showing the photodetecting section 10 having such dimensions, showing a state of the photodetecting section 10 and the imaging region 10b in the second imaging mode for panoramic radiography or cephalometric radiography. In this second imaging mode, by setting the imaging region 10b on the diagonal line of the photodetecting section 10, the width in the up-down direction can be set to 17 cm. In this case, approximately 7 mm is sufficient as the lateral width of the imaging region 10b.

However, for example, in some cases of panoramic radiography, the width in the up-down direction of the imaging region is allowed to be approximately 15 cm. Depending on the configuration of the X-ray imaging system, approximately 14 cm is also allowed. In these cases, as shown in FIG. 14, preferably, the lateral width WT of the imaging region 10b is set as wide as possible in a range in which the width in the up-down direction of the imaging region 10b becomes not less than 15 cm (or 14 cm).

Figure 14:
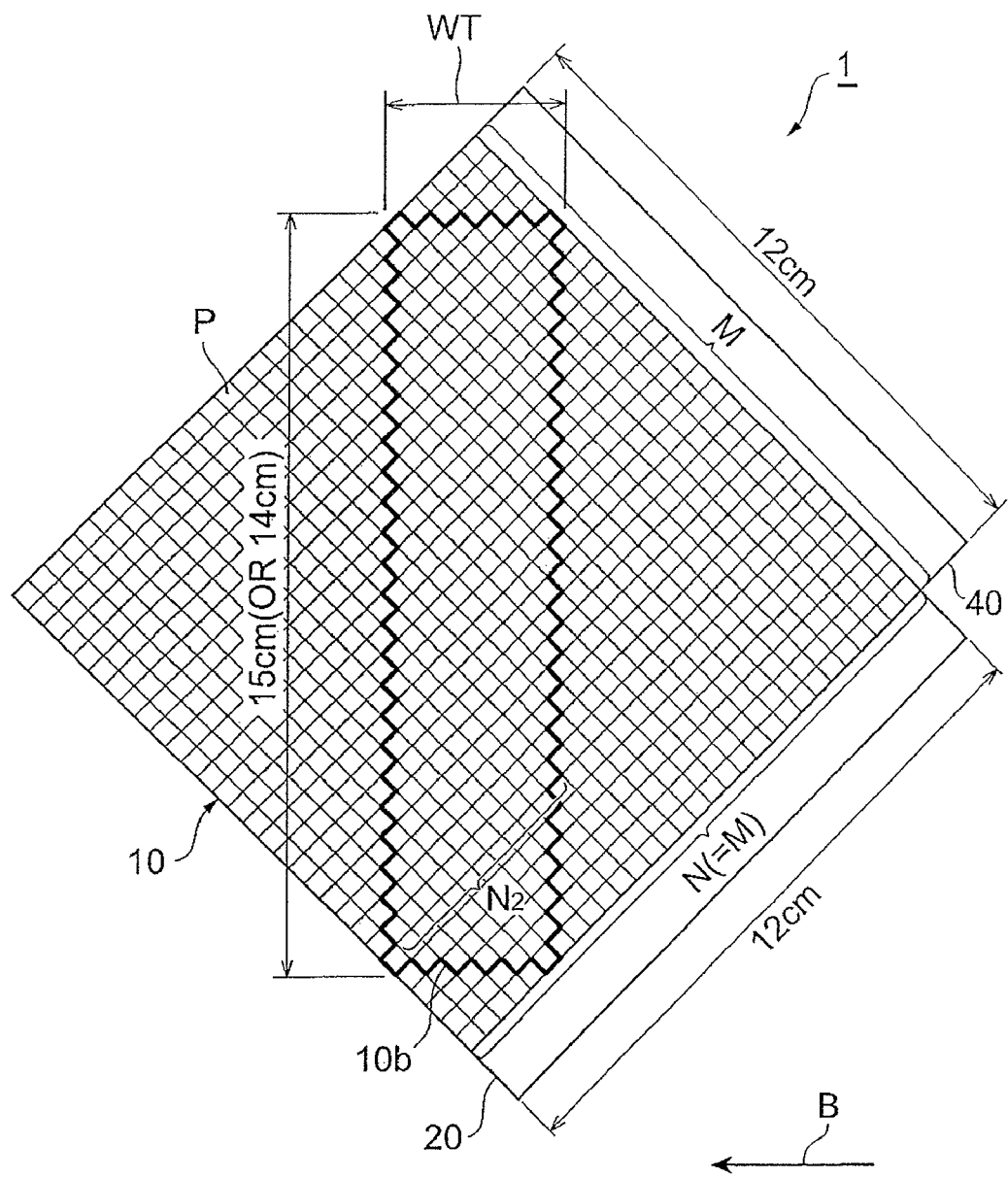
FIG. 14 is a plan view showing a square-shaped photodetecting section 10 and a planar imaging region 10b.

FIG. 14 is a plan view showing the photodetecting section 10 when the lateral width WT of the imaging region 10b is thus set to be wide. The imaging region 10b shown in FIG. 14 is composed of a plurality of pixels P described as follows. First, among the first to M-th rows of the photodetecting section 10, in several rows on one end portion including the first row, the pixels P of the imaging region 10b are set so that the number of columns gradually increases as the row number ascends around a certain column separated by several columns from the first column. In several rows at the other end portion including the M-th row, the pixels P of the imaging region 10b are set so that the number of columns gradually increase as the row number descends around a certain column separated by several columns from the N-th column (in this example, N=M). In the remaining rows of the first to M-th rows of the photodetecting section 10, the imaging region 10b is composed of the pixels P of $N_2$ columns as many as the maximum number of columns $N_2$ which compose the imaging region 106 in each row of the above-described end portions, and the position of the $N_2$ columns (for example, the leading column number) shifts by one column in each row.

In the solid-state image pick-up device 1, voltage values corresponding to charges output from the pixels P included in this imaging region 10b are selectively output by the signal reading section 20. After the solid-state image pick-up device 1 outputs image data including all pixels P, in the CPU 121 shown in FIG. 1, data corresponding to pixels P included in the imaging region 10b may be extracted. Alternatively, after the CPU 121 stores image data including all pixels P in the frame memory 122, when composing a panoramic image, the image is composed by selectively using data corresponding to pixels P included in the imaging region 10b.

As shown in FIG. 14, by setting the lateral width WT of the imaging region 10b as wide as possible while securing the width in the up-down direction of the imaging region 10b necessary in the second imaging mode, the following advantage is obtained. That is, in the second imaging mode, imaging is performed while rotating the imaging region 10b with the shorter side at the top around the subject A. In the case of the linear (one-dimensional) imaging region 10b shown in FIG. 13, the solid-state image pick-up device 1 must perform imaging operations continuously while rotating around the subject A. In this case, an X-ray is continuously irradiated onto the subject A. On the other hand, as shown in FIG. 14, by making planar (two-dimensional) the imaging region 10b by setting the lateral width of the imaging region 10b as wide as possible, the solid-state image pick-up device 1 can be stopped at each step corresponding to the lateral width WT of the imaging region 10b, and during this stop, an X-ray can be irradiated in a very short time (like a pulse) to perform imaging.

Figure 15:
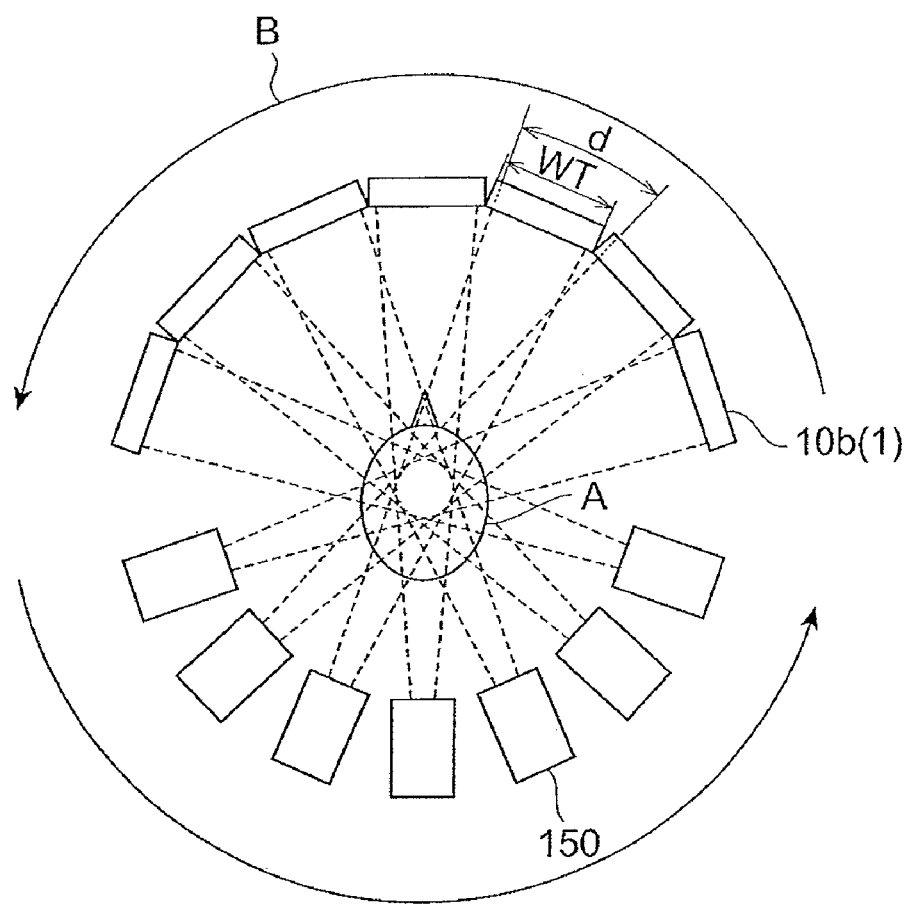
FIG. 15 is a view showing imaging by the photodetecting section 10 shown in FIG. 14 as viewed from above the subject A.

FIG. 15 is a view of this imaging from above the subject A. As shown in FIG. 15, when imaging the subject A, an X-ray source 150 and the solid-state image pick-up device 1 are disposed so as to sandwich the subject A. The X-ray source 150 is a pulse wave X-ray source which radiates a pulse X-ray in a very short time. The solid-state image pick-up device 1 is stopped at each rotation angle α corresponding to the lateral width WT of the imaging region 10b, and during this stop, the X-ray pulse is irradiated from the X-ray source 150 and imaging is performed in the solid-state image pick-up device 1. By repeating this operation, a panoramic image or cephalometric image can be acquired. According to this imaging method, while the solid-state image pick-up device 1 moves, it does not image the subject A, so that the solid-state image pick-up device can be moved at a high speed, and the time to acquire one panoramic image (or cephalometric image) can be shortened. Therefore, the time during which the examinee as the subject A must lie still is shortened, and the burden on the examinee can be reduced. In addition, the solid-state image pick-up device 1 is stopped for each imaging, so that the image can be prevented from being blurred by the motion of the subject A, and a clearer image can be acquired. Further, an X-ray is irradiated in a very short time during which the solid-state image pick-up device 1 stops and performs imaging, so that the exposure of the examinee can be further reduced.

In the imaging method shown in FIG. 15, instead of the X-ray source 150 which is a pulse wave X-ray source, a continuous wave X-ray source and a shutter which allows an X-ray emitted from the continuous wave X-ray source to pass through in a very short time may be provided. Even with this configuration, the above-described effects can be effectively obtained.

Figure 16:
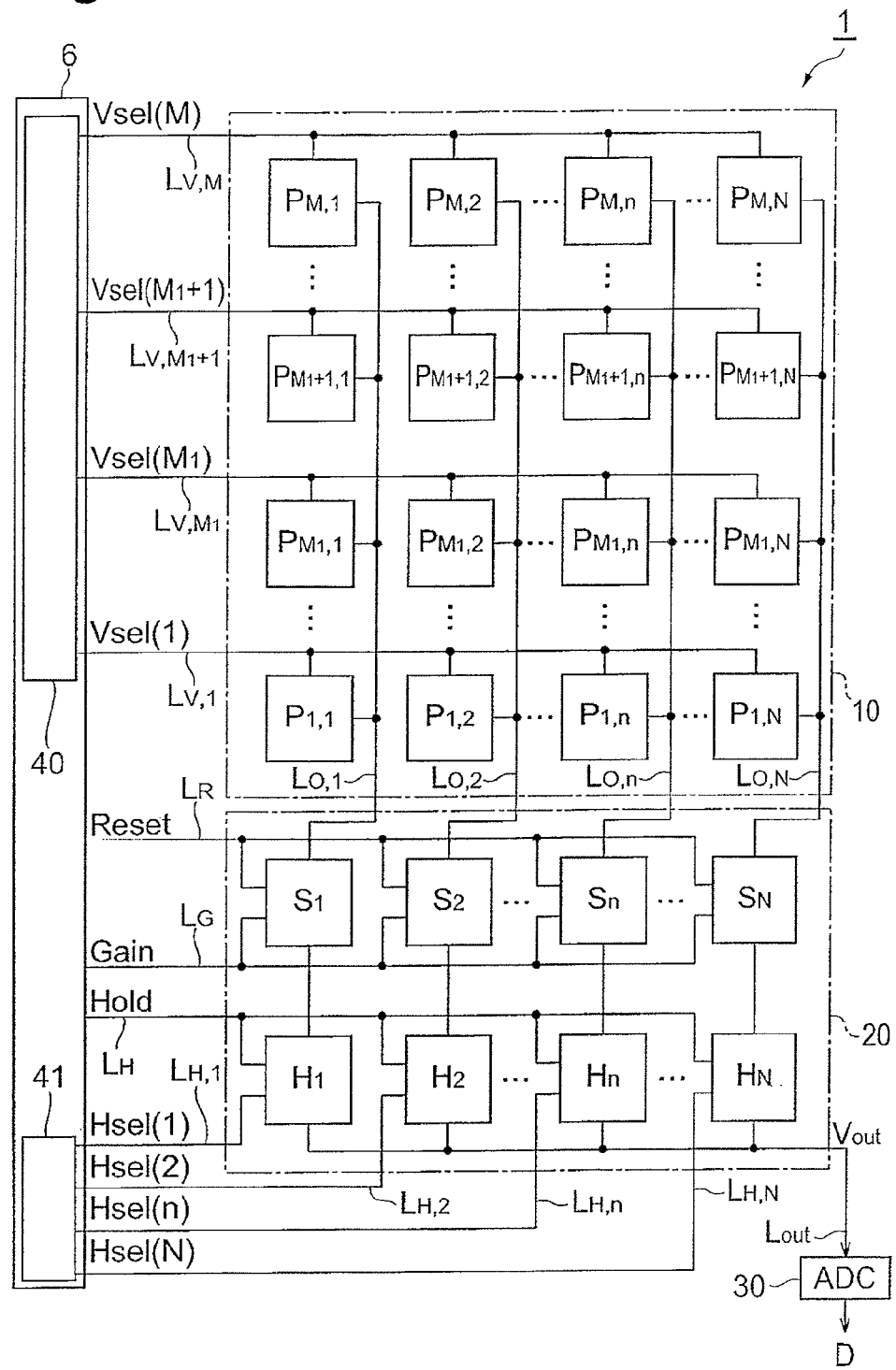
FIG. 16 is a view showing an internal configuration of the solid-state image pick-up device 1 of the first embodiment.

Subsequently, a detailed configuration of the solid-state image pick-up device 1 of the present embodiment will be described. FIG. 16 is a view showing an internal configuration of the solid-state image pick-up device 1. The photodetecting section 10 is formed by two-dimensionally aligning M×N pixels $P_{1,1}$ to $P_{M,N}$ in M rows and N columns. The pixel $P_{m,n}$ is positioned in the m-th row and the n-th column. Here, m indicates each integer not less than 1 and not more than M, and n indicates each integer not less than 1 and not more than N. The N pixels $P_{m,1}$ to $P_{m,N}$ of the m-th row are connected to the scanning shift register 40 by the m-th row selecting wire $L_{V,m}$. In FIG. 16, the scanning shift register 40 is included in the controlling section 6. The output terminals of the M pixels $P_{1,n}$ to $P_{M,n}$ of the n-th column are connected to the integrating circuit $S_n$ of the signal reading section 20 by the n-th column reading wire $L_{O,n}$.

The signal reading section 20 includes N integrating circuits $S_1$ to $S_N$ and N holding circuits $H_1$ to $H_N$. The integrating circuits $S_n$ have a common configuration. The holding circuits $H_n$ have a common configuration. Each integrating circuit $S_n$ has an input terminal connected to the reading wire $L_{O,n}$, and accumulates charges input into this input terminal, and outputs a voltage value corresponding to the accumulated charge from the output terminal to the holding circuit $H_n$. The N integrating circuits $S_1$ to $S_N$ are connected to the controlling section 6 by a resetting wire $L_R$, and connected to the controlling section 6 by a gain setting wire $L_G$. Each holding circuit $H_n$ has an input terminal connected to the output terminal of the integrating circuit $S_n$, and holds a voltage value input into this input terminal and outputs the held voltage value from the output terminal to the voltage output wire $L_{out}$. The N holding circuits $H_1$ to $H_N$ are connected to the controlling section 6 by a holding wire $L_H$. Each holding circuit $H_n$ is connected to a reading shift register 41 of the controlling section 6 by the n-th column selecting wire $L_{H,n}$.

The A/D converter 30 inputs voltage values output from the respective N holding circuits $H_1$ to $H_N$ to the voltage output wire $L_{out}$, applies A/D conversion processing to the input voltage values (analog values), and outputs digital values corresponding to the input voltage values as image data D.

The scanning shift register 40 of the controlling section 6 outputs an m-th row selecting control signal Vsel(m) to the m-th row selecting wire $L_{V,m}$, and supplies this m-th row selecting control signal Vsel(m) to the N pixels $P_{m,1}$ to $P_{m,N}$ of the m-th row. M row selecting control signals Vsel(1) to Vsel(M) are successively set to significant values. The reading shift register 41 of the controlling section 6 outputs an n-th column selecting control signal Hsel(n) to the n-th column selecting wire $L_{H,n}$ and supplies this n-th column selecting control signal Hsel(n) to the holding circuit $H_n$. N column selecting control signals Hsel(1) to Hsel(N) are also successively set to significant values.

The controlling section 6 outputs a reset control signal Reset to the resetting wire $L_R$, and supplies this reset control signal Reset to the N integrating circuits $S_1$ to $S_N$. The controlling section 6 outputs a gain setting signal Gain to the gain setting wire $L_G$, and supplies this gain setting signal Gain to the N integrating circuits $S_n$ to $S_N$. The controlling section 6 outputs a holding control signal Hold to the holding wire $L_H$, and supplies this holding control signal Hold to the N holding circuits $H_1$ to $H_N$. Further, the controlling section 6 also controls the A/D conversion processing in the A/D converter 30.

Figure 17:
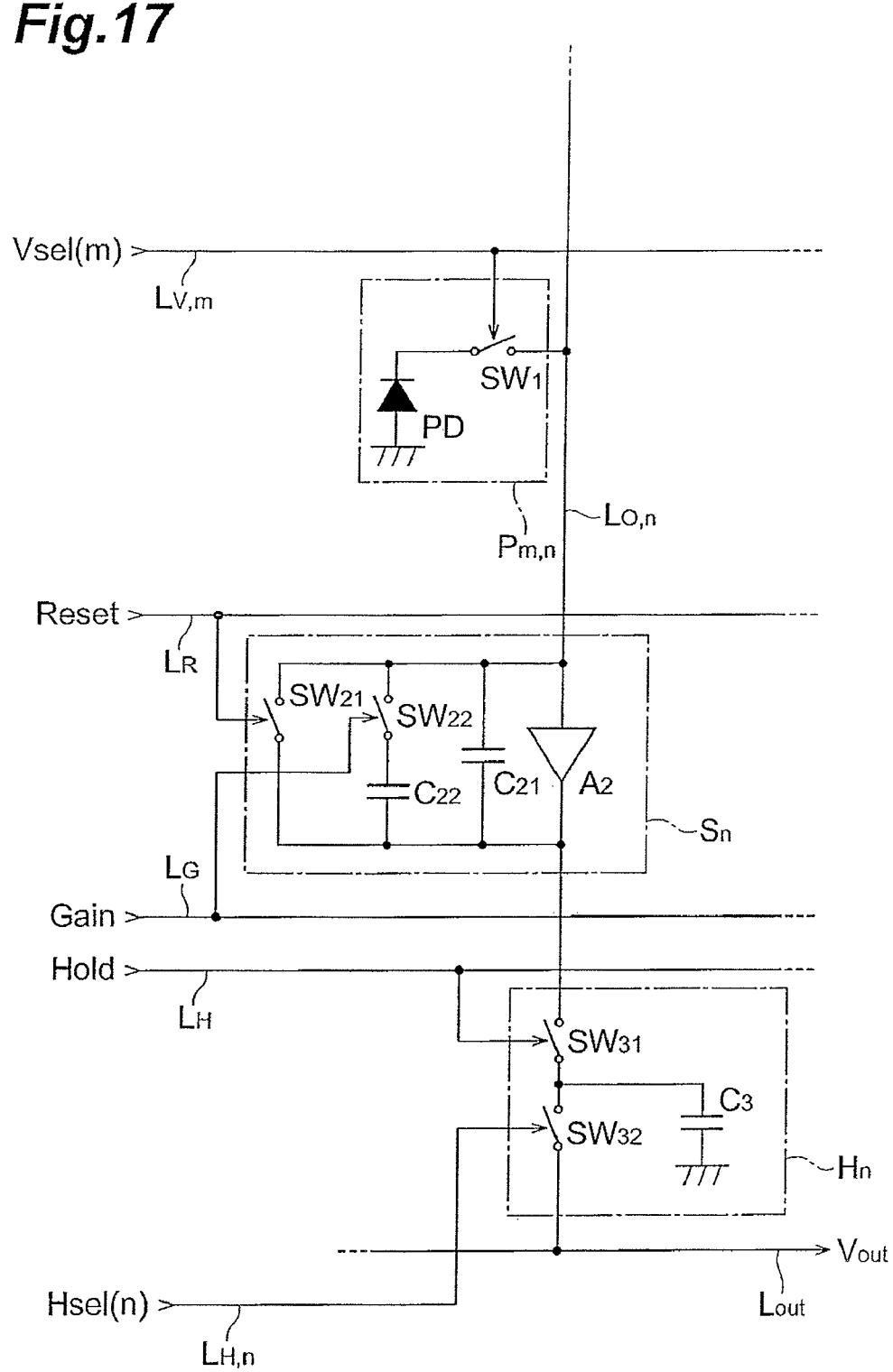
FIG. 17 is a circuit diagram of the pixel $P_{m,n}$, the integrating circuit $S_n$, and the holding circuit $H_n$ of the solid-state image pick-up device 1 of the first embodiment.

FIG. 17 is a circuit diagram of the pixel $P_{m,n}$, the integrating circuit $S_n$, and the holding circuit $H_n$ of the solid-state image pick-up device 1. Here, a circuit diagram of the pixel $P_{m,n}$ as a representative of the M×N pixels $P_{1,1}$ to $P_{M,N}$, is shown, a circuit diagram of the integrating circuit $S_n$ as a representative of the N integrating circuits $S_1$ to $S_N$, and a circuit diagram of the holding circuit $H_n$ as a representative of the N holding circuits $H_1$ to $H_N$. In other words, circuit portions relating to the pixel $P_{m,n}$ in the m-th row and the n-th column and the n-th column reading wire $L_{O,n}$ are shown.

The pixel $P_{m,n}$ includes a photodiode PD and a reading switch $SW_1$. The anode terminal of the photodiode PD is grounded, and the cathode terminal of the photodiode PD is connected to the n-th column reading wire $L_{O,n}$ via the reading switch $SW_1$. The photodiode PD generates a charge corresponding to an incident light intensity, and accumulates the generated charge in a junction capacitor. The reading switch $SW_1$ is supplied with the m-th row selecting control signal Vsel(m) through the m-th row selecting wire $L_{V,m}$ from the controlling section 6. The m-th row selecting control signal Vsel(m) instructs opening and closing operations of the reading switches $Sw_1$ of the N pixels $P_{m,1}$ to $P_{m,N}$ of the m-th row in the photodetecting section 10.

In this pixel $P_{m,n}$, when the m-th row selecting control signal Vsel(m) is at the low level, the reading switch $SW_1$ opens, and a charge generated in the photodiode PD is not output to the n-th column reading wire $L_{O,n}$ but is accumulated in the junction capacitor. On the other hand, when the m-th row selecting control signal Vsel(m) is at the high level, the reading switch $SW_1$ closes, and the charge generated in the photodiode PD and accumulated in the junction capacitor until then is output to the n-th column reading wire $L_{O,n}$ through the reading switch $SW_1$.

The n-th column reading wire $L_{O,n}$ is connected to the reading switches $SW_1$ of the M pixels $P_{1,n}$ to $P_{M,n}$ of the n-th column of the photodetecting section 10. The n-th column reading wire $L_{O,n}$ reads a charge generated in the photodiode PD of any pixel of the M pixels $P_{1,n}$ to $P_{M,n}$ via the reading switch $SW_1$ of this pixel and transfers it to the integrating circuit $S_n$.

The integrating circuit $S_n$ includes an amplifier $A_2$, an integrating capacitive element $C_{21}$, an integrating capacitive element $C_{22}$, a discharge switch $SW_{21}$, and a gain setting switch $SW_{22}$. The integrating capacitive element $C_{21}$ and the discharge switch $SW_{21}$ are connected in parallel to each other, and provided between the input terminal and the output terminal of the amplifier $A_2$. The integrating capacitive element $C_{22}$ and the gain setting switch $SW_{22}$ are connected in series to each other, and are provided between the input terminal and the output terminal of the amplifier $A_2$ so that the gain setting switch $SW_{22}$ is connected to the input terminal side of the amplifier $A_2$. The input terminal of the amplifier $A_2$ is connected to the n-th column reading wire $L_{O,n}$.

The discharge switch $SW_{21}$ is supplied with a reset control signal Reset through the resetting wire $L_R$ from the controlling section 6. The reset control signal Reset instructs opening and closing operations of the discharge switches $SW_{21}$ of the N integrating circuits $S_1$ to $S_N$. The gain setting switch $SW_{22}$ is supplied with a gain setting signal Gain through the gain setting wire $L_G$ from the controlling section 6. The gain setting signal Gain instructs opening and closing operations of the gain setting switches $SW_{22}$ of the N integrating circuits $S_1$ to $S_N$.

In this integrating circuit $S_n$, a feedback capacitor whose capacitance value is variable is composed of the integrating capacitive elements $C_{21}$ and $C_{22}$ and the gain setting switch $SW_{22}$. In other words, when the gain setting signal Gain is at the low level and the gain setting switch $SW_{22}$ is opened, the capacitance value of the feedback capacitor is equal to that of the integrating capacitive element $C_{21}$. On the other hand, when the gain setting signal Gain is at the high level and the gain setting switch $SW_{22}$ is closed, the capacitance value of the feedback capacitor is equal to a sum of the capacitance values of the integrating capacitive elements $C_{21}$ and $C_{22}$. When the reset control signal Reset is at the high level, the discharge switch $SW_{21}$ closes and the feedback capacitor is discharged, and a voltage value to be output from the integrating circuit $S_n$ is initialized. On the other hand, when the reset control signal Reset is at the low level, the discharge switch $SW_{21}$ opens and a charge input into the input terminal is accumulated in the feedback capacitor, and a voltage corresponding to the accumulated charge is output from the integrating circuit $S_n$.

The holding circuit $H_n$ includes an input switch $SW_{31}$, an output switch $SW_{32}$, and a holding capacitive element $C_3$. One end of the holding capacitive element $C_3$ is grounded. The other end of the holding capacitive element $C_3$ is connected to the output terminal of the integrating circuit $S_n$ via the input switch $SW_{31}$, and connected to a voltage output wire $L_{out}$ via the output switch $SW_{32}$. The input switch $SW_{31}$ is supplied with a holding control signal Hold through the holding wire $L_H$ from the controlling section 6. The holding control signal Hold instructs opening and closing operations of the input switches $SW_{31}$ of the N holding circuits $H_1$ to $H_N$. The output switch $SW_{32}$ is supplied with an n-th column selecting control signal Hsel(n) through the n-th column selecting wire $L_{H,n}$ from the controlling section 6. The n-th column selecting control signal Hsel(n) instructs opening and closing operations of the output switches $SW_{32}$ of the holding circuits $H_n$.

In the holding circuit $H_n$, when the holding control signal Hold changes from the high level to the low level, the input switch $SW_{31}$ changes from the closed state to an opened state, and a voltage value input in the input terminal at this time is held by the holding capacitive element $C_3$. When the n-th column selecting control signal Hsel(n) is at the high level, the output switch $SW_{32}$ closes and the voltage value held in the holding capacitive element $C_3$ is output to the voltage output wire $L_{out}$.

When outputting voltage values corresponding to received light intensities of the N pixels $P_{m,1}$ to $P_{m,N}$ of the m-th row of the photodetecting section 10, the controlling section 6 instructs the discharge switches $SW_{21}$ of the N integrating circuits $S_1$ to $S_N$ to temporarily close and then open by a reset control signal Reset, and thereafter, the controlling section instructs the reading switches $SW_1$ of the N pixels $P_{m,1}$ to $P_{m,N}$ of the m-th row of the photodetecting section 10 to close during a predetermined period by an m-th row selecting control signal Vsel(m). During this predetermined period, the controlling section 6 instructs the input switches $SW_{31}$ of the N holding circuits $H_1$ to $H_N$ to change from the closed state into an opened state by a holding control signal Hold. Then, the controlling section 6 instructs the output switches $SW_{32}$ of the N holding circuits $H_1$ to $H_N$ to successively close during a predetermined period by row selecting control signals Hsel(1) to Hsel(N). The controlling section 6 performs this control for each of the rows.

Thus, the controlling section 6 controls the opening and closing operations of the reading switches $SW_1$ of the M×N pixels $P_{1,1}$ to $P_{M,N}$ of the photodetecting section 10, and controls a voltage value holding operation and output operation in the signal reading section 20. Accordingly, the controlling section 6 repeatedly outputs voltage values corresponding to charges generated in the respective photodiodes PD of the M×N pixels $P_{1,1}$ to $P_{M,N}$ of the photodetecting section 10 as frame data from the signal reading section 20.

As described above, the solid-state image pick-up device 1 of the present embodiment has the first imaging mode for CT and the second imaging mode for panoramic radiography or cephalometric radiography. As shown in FIG. 5, the imaging region in the photodetecting section 10 is different between the first imaging mode and the second imaging mode (the region 10a of FIG. 5(a) in the first imaging mode, and the region 10b of FIG. 5(b) in the second imaging mode). Therefore, in the first imaging mode, the controlling section 6 outputs voltage values corresponding to charges generated in the respective photodiodes PD of the M×N pixels $P_{1,1}$ to $P_{M,N}$ of the photodetecting section 10 from the signal reading section 20. In the second imaging mode, the controlling section 6 selectively outputs voltage values corresponding to charges generated in the respective photodiodes PD of the pixels $P_{m,n}$ in a specific range composing the imaging region 10b among the M×N pixels $P_{1,1}$ to $P_{M,N}$ of the photodetecting section 10, from the signal reading section 20.

In the second imaging mode, in comparison with the case of the first imaging mode, the controlling section 6 makes smaller the reading pixel pitch in the frame data based on voltage values output from the signal reading section 20, and makes higher the frame rate which indicates the number of frame data to be output per unit time, and makes larger the gain as a ratio of the output voltage value to an input charge in the signal reading section 20. For example, in the first imaging mode for CT, the pixel pitch is 200 micrometers, and the frame rate is 30 F/s. In the second imaging mode for panoramic radiography or cephalometric radiography, the pixel pitch is 100 micrometers, and the frame rate is 300 F/s.

Thus, in the second imaging mode, the pixel pitch is smaller and the frame rate is higher than in the first imaging mode. Therefore, in the first imaging mode, to make larger the pixel pitch than in the second imaging mode, binning reading is necessary. In the second imaging mode, the frame rate is higher than in the first imaging mode, so that the amount of light which each pixel receives in each frame data is smaller.

Therefore, the controlling section 6 makes the gain as a ratio of the output voltage value to an input charge in the signal reading section 20 different between the first imaging mode and the second imaging mode. In other words, when each integrating circuit $S_n$ is configured as shown in FIG. 17, by controlling opening/closing of the gain setting switch $SW_{22}$ by a gain setting signal Gain, the controlling section 6 appropriately sets the capacitance value of the feedback capacitor of each integrating circuit $S_n$ to make the gain different between the first imaging mode and the second imaging mode.

In detail, in the first imaging mode, by closing the gain setting switch $SW_{22}$, the capacitance value of the feedback capacitor is made equal to the sum of the capacitance values of the integrating capacitive element $C_{21}$ and the integrating capacitive element $C_{22}$. On the other hand, in the second imaging mode, by opening the gain setting switch $SW_{22}$, the capacitance value of the feedback capacitor is made equal to the capacitance value of the integrating capacitive element $C_{21}$. By these operations, the capacitance value of the feedback capacitor of each integrating circuit $S_n$ is made smaller and the gain is made larger in the second imaging mode than in the first imaging mode. Accordingly, the pixel data with respect to a certain light amount in the first imaging mode and the second imaging mode can be made close to each other, and preferable operations can be realized in the respective imaging modes.

Next, operations of the solid-state image pick-up device 1 of the first embodiment will be described in detail. In the solid-state image pick-up device 1 of the present embodiment, under control by the controlling section 6, the M row selecting control signals Vsel(1) to Vsel(M), the N column selecting control signals Hsel(1) to Hsel(N), the reset control signal Reset, and the holding control signal Hold change their levels at respective predetermined timings, and accordingly, an optical image made incident on the photodetecting section 10 can be imaged and frame data can be obtained.

Figure 18:
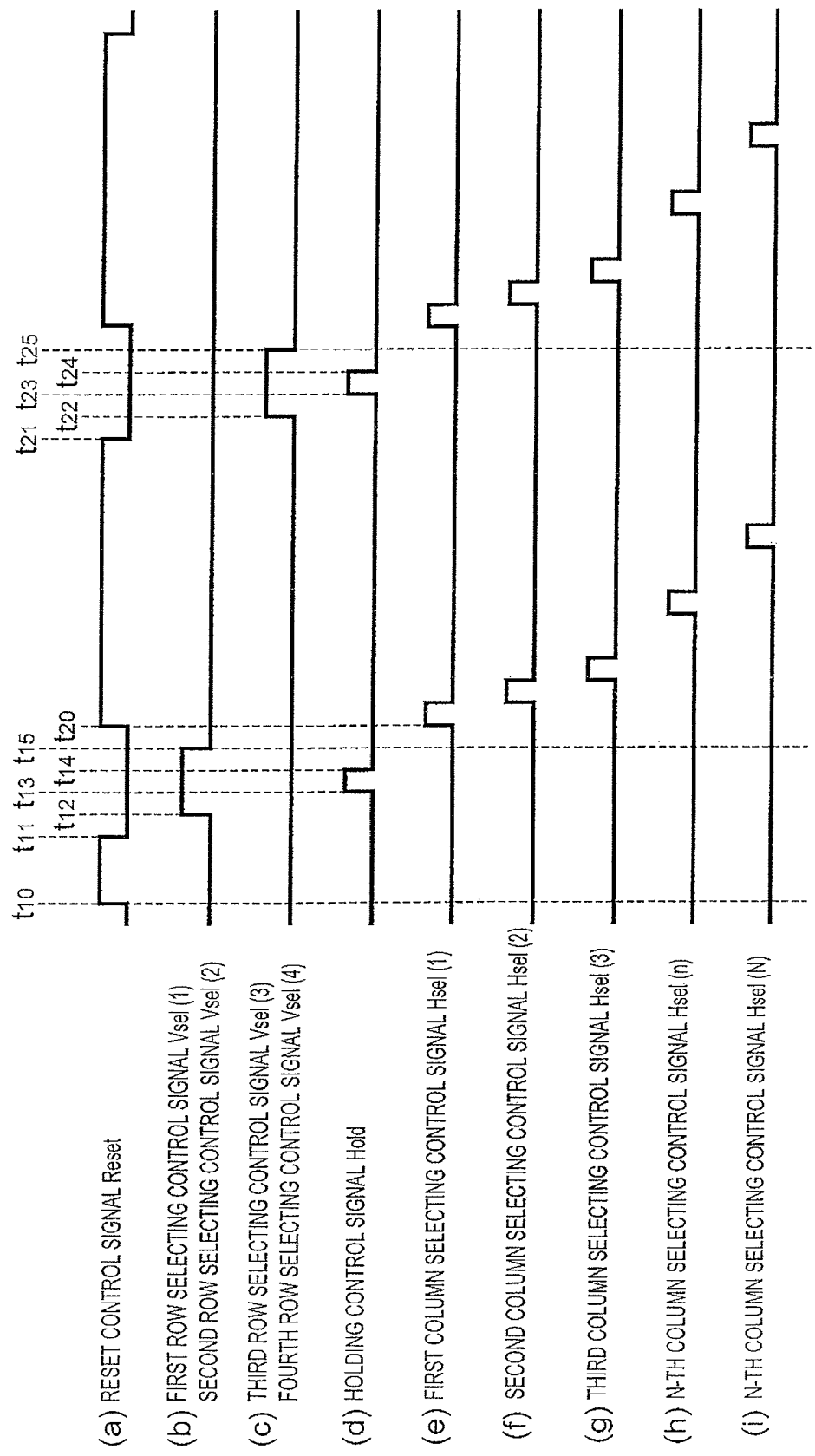
FIG. 18 is a timing chart describing operations of the solid-state image pick-up device 1 of the first embodiment.

The operations of the solid-state image pick-up device 1 in the first imaging mode are as follows. FIG. 18 is a timing chart describing operations of the solid-state image pick-up device 1 of the first embodiment. Here, operations for binning reading from 2 rows and 2 columns in the first imaging mode will be described. That is, the reading pixel pitch in the frame data is set to be twice the pitch of the pixels. In each integrating circuit $S_n$, the gain setting switch $SW_{22}$ is closed, the capacitance value of the feedback capacitor is set to a large value, and the gain is set to a small value.

This timing chart shows, in order from the top, (a) a reset control signal Reset for instructing opening and closing operations of the discharge switches $SW_{21}$ of the N integrating circuits $S_1$ to $S_N$, (b) a first row selecting control signal Vsel(1) and a second row selecting control signal Vsel(2) for instructing opening and closing operations of the reading switches $SW_1$ of the pixels $P_{1,1}$ to $P_{1,N}$ and $P_{2,1}$ to $P_{2,N}$ of the first row and second row of the photodetecting section 10, (c) a third row selecting control signal Vsel(3) and a fourth row selecting control signal Vsel(4) for instructing opening and closing operations of the reading switches $SW_1$ of the pixels $P_{3,1}$ to $P_{3,N}$ and $P_{4,1}$ to $P_{4,N}$ of the third and fourth rows of the photodetecting section 10, and (d) a holding control signal Hold for instructing opening and closing operations of the input switches $SW_{31}$ of the N holding circuits $H_1$ to $H_N$.

Subsequently, this timing chart further shows (e) a first column selecting control signal Hsel(1) for instructing opening and closing operations of the output switch $SW_{32}$ of the holding circuit $H_1$, (f) a second column selecting control signal Hsel(2) for instructing opening and closing operations of the output switch $SW_{32}$ of the holding circuit $H_2$, (g) a third column selecting control signal Hsel(3) for instructing opening and closing operations of the output switch $SW_{32}$ of the holding circuit $H_3$, (h) an n-th column selecting control signal Hsel(n) for instructing opening and closing operations of the output switch $SW_{32}$ of the holding circuit $H_n$, and (i) an N-th column selecting control signal Hsel(N) for instructing opening and closing operations of the output switch $SW_{32}$ of the holding circuit $H_N$.

The charges which were generated in the photodiodes PD of the 2N pixels $P_{1,1}$ to $P_{1,N}$ and $P_{2,1}$ to $P_{2,N}$ of the first row and second rows and accumulated in the junction capacitors are read as follows. Before the timing $t_{10}$, the M row selecting control signals Vsel(1) to Vsel(M), N column selecting control signals Hsel(1) to Hsel(N), the reset control signal Reset, and the holding control signal Hold are at the low level.

During the period from the timing $t_{10}$ to the timing $t_{11}$, the reset control signal Reset to be output from the controlling section 6 to the resetting wire $L_R$ becomes the high level, and accordingly, in the N integrating circuits $S_1$ to $S_N$, the discharge switches $SW_{21}$ close and the integrating capacitive elements $C_{21}$ and $C_{22}$ are discharged. During the period from the timing $t_{12}$ to the timing $t_{15}$ after the timing $t_{11}$, the first row selecting control signal Vsel(1) to be output to the first row selecting wire $L_{V,1}$ from the controlling section 6 becomes the high level, and accordingly, the reading switches $SW_1$ of the N pixels $P_{1,1}$ to $P_{1,N}$ of the first row of the photodetecting section 10 close. During the same period ($t_{12}$ to $t_{15}$), the second row selecting control signal Vsel(2) to be output from the controlling section 6 to the second row selecting wire $L_{V,2}$ becomes the high level, and accordingly, the reading switches $SW_1$ of the N pixels $P_{2,1}$ to $P_{2,N}$ of the second row of the photodetecting section 10 close.

During a period from the timing $t_{13}$ to the timing $t_{14}$ in this period ($t_{12}$ to $t_{15}$), the holding control signal Hold to be output from the controlling section 6 to the holding wire $L_H$ becomes the high level, and accordingly, the input switches $SW_{31}$ of the N holding circuits $H_1$ to $H_N$ close.

During the period ($t_{12}$ to $t_{15}$), the reading switches $SW_1$ of the pixels $P_{1,n}$ and $P_{2,n}$ of the first row and second row close, and the discharge switches $SW_{21}$ of the integrating circuits $S_n$ open. Therefore, charges which were generated in the photodiodes PD of the pixels $P_{1,n}$ and accumulated in the junction capacitors until then are transferred to and accumulated in the integrating capacitive elements $C_{21}$ and $C_{22}$ of the integrating circuits $S_n$ through the reading switches $SW_1$ of the pixels $P_{1,n}$ and the n-th column reading wires $L_{O,n}$. Concurrently, charges which were generated in the photodiodes PD of the pixels $P_{2,n}$ and accumulated in the junction capacitors until then are also transferred to and accumulated in the integrating capacitive elements $C_{21}$ and $C_{22}$ of the integrating circuits $S_n$ through the reading switches $SW_1$ of the pixels $P_{2,n}$ and the n-th column reading wires $L_{O,n}$. Then, voltage values corresponding to the charges accumulated in the integrating capacitive elements $C_{21}$ and $C_{22}$ of the integrating circuits $S_n$ are output from the output terminals of the integrating circuits $S_n$.

At the timing $t_{14}$ in the period ($t_{12}$ to $t_{15}$), the holding control signal Hold changes from the high level to the low level, and accordingly, in the N holding circuits $H_1$ to $H_N$, the input switches $SW_{31}$ change from the closed state to the opened state, and voltage values which were output from the output terminals of the integrating circuits $S_n$ and input to the input terminals of the holding circuits $H_n$ at this time are held in the holding capacitive elements $C_3$.

Then, after the period ($t_{12}$ to $t_{15}$), the column selecting control signals Hsel(1) to Hsel(N) output from the controlling section 6 to the column selecting wires $L_{H,1}$ to $L_{H,N}$ successively become the high level during a predetermined period, and accordingly, the output switches $SW_{32}$ of the N holding circuits $H_1$ to $H_N$ successively close during the predetermined period, and voltage values held in the holding capacitive elements $C_3$ of the holding circuits $H_n$ are successively output to the voltage output wire $L_{out}$ through the output switches $SW_{32}$. The voltage values $V_{out}$ to be output to the voltage output wire $L_{out}$ represent values obtained by summing-up received light intensities in the photodiodes PD of the 2N pixels $P_{1,1}$ to $P_{1,N}$ and $P_{2,1}$ to $P_{2,N}$ of the first row and the second row, respectively, in the column direction.

The voltage values successively output from the N holding circuits $H_1$ to $H_N$ are input into the A/D converter 30 and converted into digital values corresponding to the input voltage values. Then, among the N digital values output from the A/D converter 30, digital values corresponding to the first column and the second column are summed up, the digital values corresponding to the third column and the fourth column are summed up, and similarly, each two subsequent digital values are summed up.

Subsequently, charges which were generated in the photodiodes PD of the 2N pixels $P_{3,1}$ to $P_{3,N}$ and $P_{4,1}$ to $P_{4,N}$ of the third row and the fourth row and accumulated in the junction capacitors are read as follows.

In the above-described operation, during the period from the timing $t_{20}$ at which the column selecting control signal Hsel(1) becomes the high level to the timing $t_{21}$ after the timing at which the column selecting control signal Hsel(N) temporarily becomes the high level and then becomes the low level, the reset control signal Reset to be output from the controlling section 6 to the resetting wire $L_R$ becomes the high level, and accordingly, in the N integrating circuits $S_1$ to $S_N$, the discharge switches $SW_{21}$ close and the integrating capacitive elements $C_{21}$ and $C_{22}$ are discharged. During the period from the timing $t_{22}$ after the timing $t_{21}$ to the timing $t_{25}$, the third row selecting control signal Vsel(3) to be output from the controlling section 6 to the third row selecting wire $L_{V,3}$ becomes the high level, and accordingly, the reading switches $SW_1$ of the N pixels $P_{3,1}$ to $P_{3,N}$ of the third row of the photodetecting section 10 close. During the same period ($t_{22}$ to $t_{25}$), the fourth row selecting control signal Vsel(4) to be output from the controlling section 6 to the fourth row selecting wire $L_{V,4}$ becomes the high level, and accordingly, the reading switches $SW_1$ of the N pixels $P_{4,1}$ to $P_{4,N}$ of the fourth row of the photodetecting section 10 close.

In this period ($t_{22}$ to $t_{25}$), during a period from the timing $t_{23}$ to the timing $t_{24}$, the holding control signal Hold to be output from the controlling section 6 to the holding wire $L_H$ becomes the high level, and accordingly, the input switches $SW_{31}$ in the N holding circuits $H_1$ to $H_N$ close.

Then, after the period ($t_{22}$ to $t_{25}$), the column selecting control signals Hsel(1) to Hsel(N) to be output from the controlling section 6 to the column selecting wires $L_{H,1}$ to $L_{H,N}$ successively become the high level during a predetermined period, and accordingly, the output switches $SW_{32}$ of the N holding circuits $H_1$ to $H_N$ successively close during the predetermined period. Accordingly, voltage values $V_{out}$ representing values obtained by summing up in the column direction the received light intensities in the photodiodes PD of the 2N pixels $P_{3,1}$ to $P_{3,N}$ and $P_{4,1}$ to $P_{4,N}$ of the third row and the fourth row are output to the voltage output wire $L_{out}$.

The voltage values successively output from the N holding circuits $H_1$ to $H_N$ are input into the A/D converter 30, and converted into digital values corresponding to the input voltage values. Then, among the N digital values output from the A/D converter 30, digital values corresponding to the first column and the second column are summed up, the digital values corresponding to the third column and the fourth column are summed up, and similarly, each two subsequent digital values are summed up.

In the first imaging mode, subsequent to the above-described operation for the first row and the second row and subsequent operation for the third row and the fourth row, the same operation is performed for the fifth row to the M-th row, and accordingly, frame data representing an image obtained by one imaging is obtained. When the operation for the M-th row is finished, the same operation is performed again in the range from the first row to the M-th row, and frame data representing a next image is obtained. Thus, by repeating the same operation with a predetermined period, the voltage values $V_{out}$ showing a two-dimensional intensity distribution of an optical image received by the photodetecting section 10 are output to the voltage output wire $L_{out}$, and frame data is repeatedly obtained. The reading pixel pitch in the frame data obtained in this case is twice the pitch of the pixels.

On the other hand, operations of the solid-state image pick-up device 1 in the second imaging mode are as follows.

Figure 19:
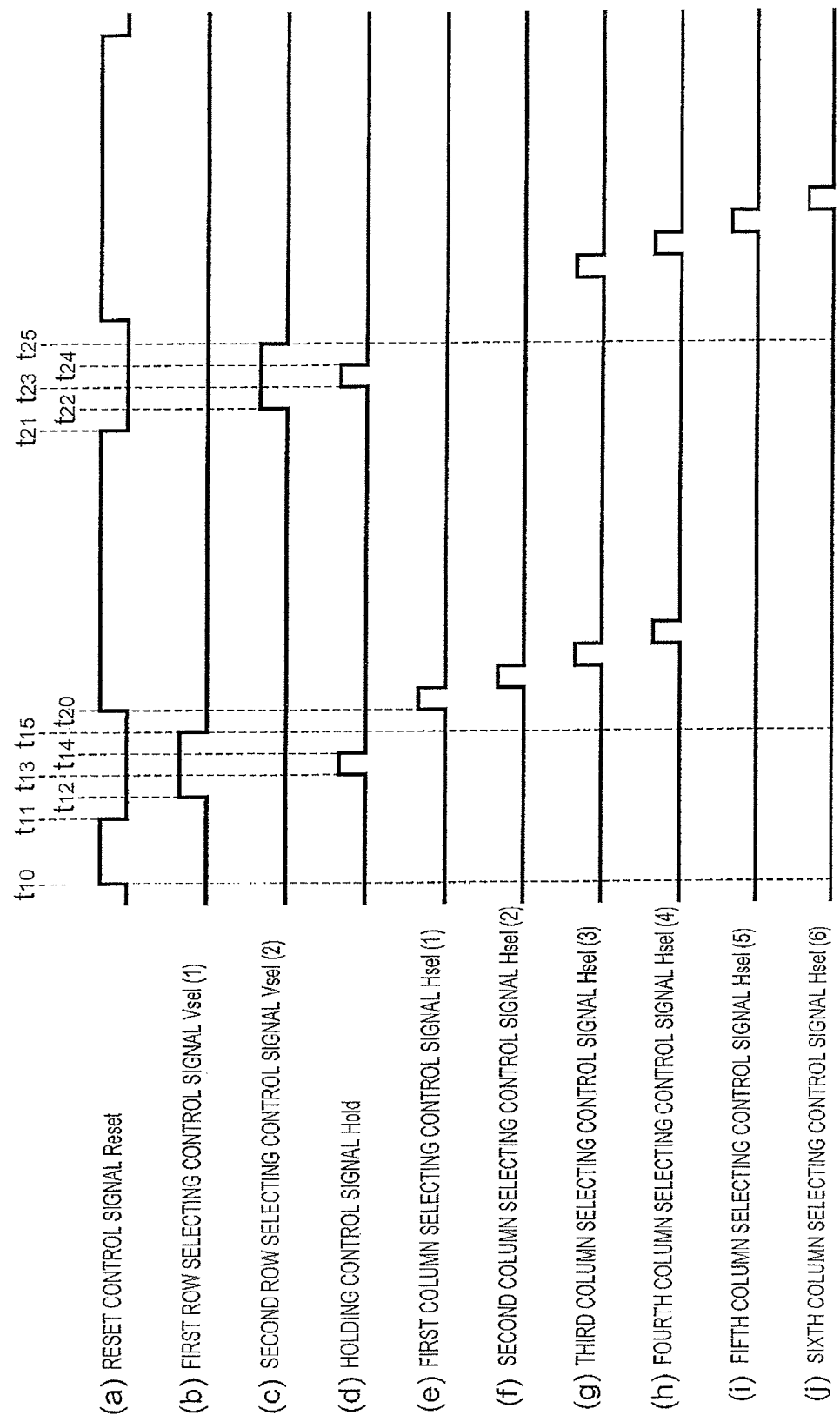
FIG. 19 is a timing chart describing operations of the solid-state image pick-up device 1 of the first embodiment.

FIG. 19 is the timing chart describing operations of the solid-state image pick-up device 1 of the first embodiment. In this second imaging mode, binning reading is not performed. In other words, the reading pixel pitch in the frame data is set equally to the pitch of the pixels. In each integrating circuit $S_n$, the gain setting switch $SW_{22}$ is opened, the capacitance value of the feedback capacitor is set to a small value, and the gain is set to a large value.

FIG. 19 shows operations for the first row and the second row of the photodetecting section 10. This figure shows, in order from the top, (a) a reset control signal Reset, (b) a first row selecting control signal Vsel(1), (c) a second row selecting control signal Vsel(2), (d) a holding control signal Hold, (e) a first column selecting control signal Hsel(1), (f) a second column selecting control signal Hsel(2), (g) a third column selecting control signal Hsel(3), (h) a fourth column selecting control signal Hsel(4), (i) a fifth column selecting control signal Hsel(5), and (j) a sixth column selecting control signal Hsel(6).

Charges which were generated in the photodiodes PD of the N pixels $P_{1,1}$ to $P_{1,N}$ of the first row and accumulated in the junction capacitors are read as follows. Before the timing $t_{10}$, the M row selecting control signals Vsel(1) to Vsel(M), the N column selecting control signals Hsel(1) to Hsel(N), the reset control signal Reset, and the holding control signal Hold are at the low level.

During the period from the timing $t_{10}$ to the timing $t_{11}$, the reset control signal Reset to be output from the controlling section 6 to the resetting wire $L_R$ becomes the high level, and accordingly, in the N integrating circuits $S_1$ to $S_N$, the discharge switches $SW_{21}$ close, and the integrating capacitive elements $C_{21}$ are discharged. During a period from the timing $t_{12}$ after the timing $t_{11}$ to the timing $t_{15}$ the first row selecting control signal Vsel(1) to be output from the controlling section 6 to the first row selecting wire $L_{V,1}$ becomes the high level, and accordingly, the reading switches $SW_1$ of the N pixels $P_{1,1}$ to $P_{1,N}$ of the first row of the photodetecting section 10 close.

In this period ($t_{12}$ to $t_{15}$), during the period from the timing $t_{13}$ to the timing $t_{14}$, the holding control signal Hold to be output from the controlling section 6 to the holding wire $L_H$ becomes the high level, and accordingly, the input switches $SW_{31}$ in the N holding circuits $H_1$ to $H_N$ close.

During the period ($t_{12}$ to $t_{15}$), the reading switches $SW_1$ of the pixels $P_{1,n}$ of the first row close, and the discharge switches $SW_{21}$ of the integrating circuits $S_n$ open, so that the charges which were generated in the photodiodes PD of the pixels $P_{1,n}$ and accumulated in the junction capacitors until then are transferred to and accumulated in the integrating capacitive elements $C_{21}$ of the integrating circuits $S_n$ through the reading switches $SW_1$ of the pixels $P_{1,n}$ and the n-th column reading wires $L_{O,n}$. Then, voltage values corresponding to charges accumulated in the integrating capacitive elements $C_{21}$ of the integrating circuits $S_n$ are output from the output terminals of the integrating circuits $S_n$.

At the timing $t_{14}$ in the period ($t_{12}$ to $t_{15}$), the holding control signal Hold changes from the high level to the low level, and accordingly, in the N holding circuits $H_1$ to $H_N$, the input switches $SW_{31}$ change from the closed state to the opened state, and voltage values which are output from the output terminals of the integrating circuits $S_n$ and input in the input terminals of the holding circuits $H_n$ are held in the holding capacitive elements $C_3$.

Then, after the period ($t_{12}$ to $t_{15}$), among the column selecting control signals Hsel(1) to Hsel(N) to be output from the controlling section 6 to the column selecting wires $L_{H,1}$ to $L_{H,N}$, the column selecting control signals Hsel(1) to Hsel ($N_1$) corresponding to first continuous $N_1$ rows ($N_1$=4 in this embodiment) successively become the high level during a predetermined period. Accordingly, output switches $SW_{32}$ of the holding circuits $H_1$ to $H_{N1}$ of the first continuous $N_1$ columns successively close during the predetermined period, and voltage values held in the holding capacitive elements $C_3$ of the holding circuits $H_n$ are successively output to the voltage output wire $L_{out}$ through the output switches $SW_{32}$. The voltage values $V_{out}$ to be output to the voltage output wire $L_{out}$ represent received light intensities in the photodiodes PD of the $N_1$ pixels $P_{1,1}$ to $P_{1,N1}$ of the first row.

Subsequently, charges which were generated in the photodiodes PD of the N pixels $P_{2,1}$ to $P_{2,N}$ of the second row and accumulated in the junction capacitors are read as follows.

In the above-described operation, during a period from the timing $t_{20}$ at which the column selecting control signal Hsel(1) becomes the high level to the timing $t_{21}$ after the timing at which the column selecting control signal Hsel($N_1$) temporarily becomes the high level and then changes to the low level, the reset control signal Reset to be output from the controlling section 6 to the resetting wire $L_R$ becomes the high level, and accordingly, in the N integrating circuits $S_1$ to $S_N$, the discharge switches $SW_{21}$ close and the integrating capacitive elements $C_{21}$ are discharged. During a period from the timing $t_{22}$ after the timing $t_{21}$ to the timing $t_{25}$, the second row selecting control signal Vsel(2) to be output from the controlling section 6 to the second row selecting wire $L_{V,2}$ becomes the high level, and accordingly, the reading switches $SW_1$ of the N pixels $P_{2,1}$ to $P_{2,N}$ of the second row of the photodetecting section 10 close.

In this period ($t_{22}$ to $t_{25}$), during the period from the timing $t_{23}$ to the timing $t_{24}$, the holding control signal Hold to be output from the controlling section 6 to the holding wire $L_H$ becomes the high level, and accordingly, in the N holding circuits $H_1$ to $H_N$, the input switches $SW_3$, close. After the period ($t_{22}$ to $t_{25}$), among the column selecting control signals Hsel(1) to Hsel(N) to be output from the controlling section 6 to the column selecting wires $L_{H,1}$ to $L_{H,N}$, column selecting control signals Hsel(3) to Hsel($N_1$+2) corresponding to columns which are continuous $N_1$ columns and are shifted by a predetermined number of columns (two columns in this embodiment) from the $N_1$ columns of the first row successively become the high level during a predetermined period. Accordingly, the output switches $SW_{32}$ of the $N_1$ holding circuits $H_3$ to $H_{N1+2}$ close during the predetermined period. Accordingly, voltage values $V_{out}$ representing received light intensities in the photodiodes PD of the $N_1$ pixels $P_{2,3}$ to $P_{2,N1+2}$ of the second row are output to the voltage output wire $L_{out}$.

In the second imaging mode, subsequent to the above-described operation for the first row and second row, the same operation is performed for the third row to the M-th row while shifting the position of the continuous $N_1$ columns from which voltage values are to be output by the predetermined number of columns in each row to obtain frame data representing an image obtained by one imaging. When the operation for the M-th row is finished, the same operation is performed again in the range from the first row to the M-th row, and frame data representing a next image is obtained. Thus, by repeating the same operation with a predetermined period, voltage values $V_{out}$ representing a two-dimensional intensity distribution of the optical image received by the photodetecting section 10 are output to the voltage output wire $L_{out}$, and frame data is repeatedly obtained.

In the present embodiment, it is also adoptable that, to read pixel data at a high speed, the signal reading section 20 and the A/D converter 30 are divided into a plurality of groups, and pixel data are output in parallel to each other from the groups.

Figure 20:
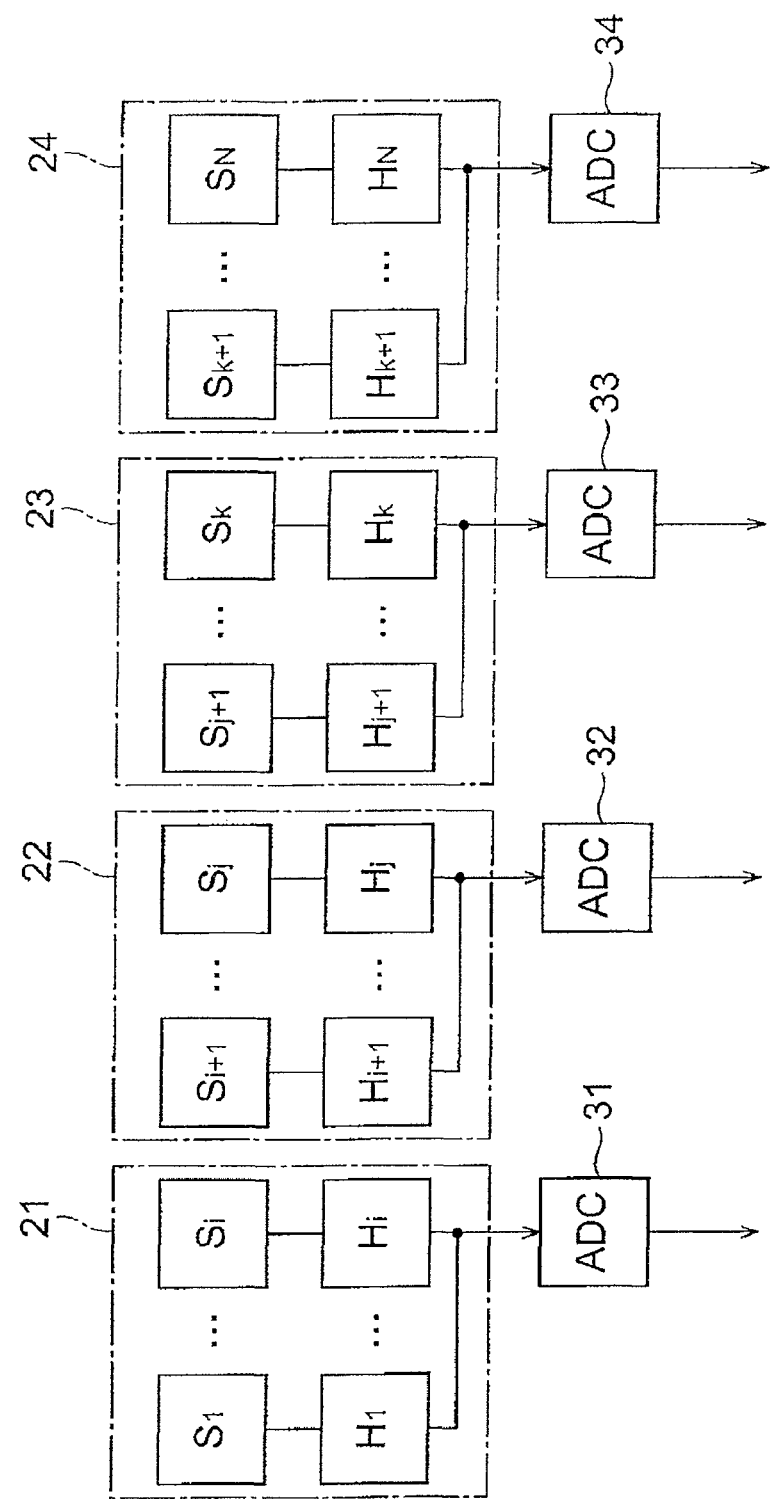
FIG. 20 is a diagram showing an exemplary variation of the configuration of the solid-state image pick-up device 1 of the first embodiment.

For example, as shown in FIG. 20, N integrating circuits $S_1$ to $S_N$ and N holding circuits $H_1$ to $H_N$ are divided into four groups, and a signal reading section 21 consisting of the integrating circuits $S_1$ to $S_i$ and the holding circuits $H_1$ to $H_i$ is set as a first group, a signal reading section 22 consisting of the integrating circuits $S_{i+1}$ to $S_j$ and the holding circuits $H_{i+1}$ to $H_j$ is set as a second group, a signal reading section 23 consisting of the integrating circuits $S_{j+1}$ to $S_k$ and the holding circuits $H_{j+1}$ to $H_k$ is set as a third group, and a signal reading section 24 consisting of the integrating circuits $S_{k+1}$ to $S_N$ and the holding circuits $H_{k+1}$ to $H_N$ is set as a fourth group. Here, "$1<i<j<k<N$" is satisfied. Voltage values successively output from the holding circuits $H_1$ to $H_i$ of the signal reading section 21 are converted into digital values by an A/D converter 31, voltage values successively output from the holding circuits $H_{i+1}$ to $H_j$ of the signal reading section 22 are converted into digital values by the A/D converter 32, voltage values successively output from the holding circuits $H_{j+1}$ to $H_k$ of the signal reading section 23 are converted into digital signals by an A/D converter 33, and voltage values successively output from the holding circuits $H_{k+1}$ to $H_N$ of the signal reading section 24 are converted into digital values by the A/D converter 34. A/D conversion processings in the four A/D converters 31 to 34 are performed in parallel to each other. Accordingly, pixel data can be read at a high speed.

For example, in consideration of binning reading from the two rows and two columns, it is also preferable that the holding circuits corresponding to odd-numbered columns among the N holding circuits $H_1$ to $H_N$ are set as a first group, holding circuits corresponding to even-numbered columns are set as a second group, and A/D converters are provided individually for the first group and the second group, and these two A/D converters are operated in parallel to each other. In this case, from the holding circuits corresponding to the odd-numbered columns and the holding circuits corresponding to the even-numbered columns, voltage values are output concurrently, and these two voltage values are A/D converted into digital values, concurrently. When binning processing is applied, these two digital values are summed up. Pixel data can also be read at a high speed in this case.

Scanning processing in the column direction of the scanning shift register 40 cannot be divided in the above-described manner. In the scanning processing in the column direction, pixels from the first pixel to the final pixel must be scanned in order. Therefore, by setting the number of columns N to be larger than the number of rows M in the solid-state image pick-up device 1, the effect of speeding up the reading by dividing the signal reading section as described above can be more satisfactorily obtained.

The medical X-ray imaging system of the present invention is not limited to the above-described embodiment, and other various variations are possible. For example, in the above-described embodiment, as an imaging region in the second imaging mode, an imaging region which tilts with respect to both of the row direction and the column direction of the photodetecting section and has a longitudinal direction in the direction orthogonal to the movement direction of the solid-state image pick-up device is illustrated, however, a region other than this can be used as the imaging region in the second imaging mode, or the entire surface of the photodetecting section can be used as the imaging region. Also in the first imaging mode, without limiting to the form in which the entire surface of the photodetecting section is used as the imaging region as in the above-described embodiment, an arbitrary region in the photodetecting section may be used as the imaging region as appropriate.

What is claimed is:

1. A medical X-ray imaging system which comprises a solid-state image pick-up device for imaging an X-ray image while moving around a jaw of an examinee, and has at least two imaging modes, wherein
   the solid-state image pick-up device includes:
   a photodetecting section having a rectangular photodetecting surface formed by two-dimensionally aligning M×N pixels (M and N are integers not less than 2) including photodiodes respectively, in M rows and N columns;
   N reading wires each of which is disposed for each of the columns and connected to the photodiodes included in the pixels of the corresponding column via reading switches;
   a signal reading section which holds voltage values corresponding to charges input through the reading wires and outputs the held voltage values successively;
   a controlling section which controls opening and closing operations of the reading switches of the respective pixels, and controls the voltage value output operation in the signal reading section to output voltage values corresponding to the charges generated in the photodiodes of the respective pixels from the signal reading section; and
   a scintillator which generates scintillation light in response to an incident X-ray and converts the X-ray image into an optical image, and outputs the optical image to the photodetecting section, and
   the medical X-ray imaging system further comprises:
   a rotation controlling section which supports the solid-state image pick-up device rotatably around an axis line perpendicular to the photodetecting surface, and controls a rotation angle of the solid-state image pick-up device so that, in one imaging mode of the two imaging modes, either a row direction or a column direction of the photodetecting section is along a movement direction of the solid-state image pick-up device, and in the other imaging mode of the two imaging modes, both of the row direction and the column direction of the photodetecting section tilt with respect to the movement direction of the solid-state image pick-up device,
   wherein in comparison with one imaging mode, in the other imaging mode, the controlling section makes smaller a reading pixel pitch in frame data based on voltage values output from the signal reading section, makes higher a frame rate which is a number of frame data to be output per unit time, and makes larger the gain which is a ratio of an output voltage value to an input charge amount in the signal reading section.

2. The medical X-ray imaging system according to claim 1, wherein
   the controlling section controls an output operation of the signal reading section so that voltage values are selectively read from the pixels forming an imaging region whose longitudinal direction is in a predetermined direction among the M×N pixels in the other imaging mode, and
   the predetermined direction tilts with respect to both of the row direction and the column direction of the photodetecting section and intersects the movement direction of the solid-state image pick-up device.

3. The medical X-ray imaging system according to claim 2, wherein
   the predetermined direction is orthogonal to the movement direction of the solid-state image pick-up device.

4. The medical X-ray imaging system according to claim 2, wherein
the imaging region is a region on a diagonal line of the photodetecting section.

5. The medical X-ray imaging system according to claim 2, wherein when the controlling section controls the output operation of the signal reading section in the other imaging mode, among voltage values held corresponding to the respective N rows of the photodetecting section, voltage values held corresponding to continuous $N_1$ columns ($N_1 < N$) are output from the signal reading section, and a position of the $N_1$ columns in the photodetecting section shifts by a predetermined number of columns each time of reading a voltage value corresponding to one or a plurality of lines.

6. The medical X-ray imaging system according to claim 1, wherein the number of rows M is smaller than the number of columns N in the photodetecting section, and the photodetecting surface has a rectangular shape whose longitudinal direction is in the row direction.

7. The medical X-ray imaging system according to claim 1, wherein
a rotation center of the solid-state image pick-up device is positioned at one of four corners of the rectangular photodetecting section, and
the solid-state image pick-up device rotates so that the one corner is positioned at a lower jaw side with respect to the examinee in both of the two imaging modes.

8. The medical X-ray imaging system according to claim 1, wherein the one imaging mode is an imaging mode for CT in dental X-ray photography, and the other imaging mode is an imaging mode for panoramic radiography in dental X-ray photography.

* * * * *